United States Patent
Uber, III

(10) Patent No.: US 11,986,621 B2
(45) Date of Patent: May 21, 2024

(54) SYNTHETIC MAGNETIC RESONANCE IMAGING AND MAGNETIC RESONANCE FINGERPRINTING WITH A CONTRAST AGENT, AND DETERMINATION OF A CONTRAST AGENT INJECTION PROTOCOL

(71) Applicant: BAYER HEALTHCARE LLC, Whippany, NJ (US)

(72) Inventor: Arthur E. Uber, III, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 575 days.

(21) Appl. No.: 16/462,410

(22) PCT Filed: Nov. 21, 2017

(86) PCT No.: PCT/US2017/062768
§ 371 (c)(1),
(2) Date: May 20, 2019

(87) PCT Pub. No.: WO2018/098144
PCT Pub. Date: May 31, 2018

(65) Prior Publication Data
US 2019/0365982 A1 Dec. 5, 2019

Related U.S. Application Data

(60) Provisional application No. 62/425,303, filed on Nov. 22, 2016.

(51) Int. Cl.
*G16H 30/40* (2018.01)
*A61B 5/055* (2006.01)
(Continued)

(52) U.S. Cl.
CPC ............ *A61M 5/007* (2013.01); *A61B 5/055* (2013.01); *A61B 6/481* (2013.01); *G01R 33/543* (2013.01);
(Continued)

(58) Field of Classification Search
CPC .......... A61M 5/007; A61M 2205/3303; A61M 2205/3379; A61M 2205/50; G16H 30/40;
(Continued)

(56) References Cited

U.S. PATENT DOCUMENTS 5,840,026 A 11/1998 Uber, III et al.
6,055,985 A 5/2000 Bae et al.
(Continued)

FOREIGN PATENT DOCUMENTS

JP 2000506398 A 5/2000
JP 4417621 B2 2/2010
(Continued)

OTHER PUBLICATIONS

Anderson et al. Dual Contrast-Magnetic Resonance Fingerprinting (DC-MRF): A Platform for Simultaneous Quantification of Multiple MRI Contrast Agents, Aug. 16, 2017, Nature—Scientific Reports (Year: 2017).*
(Continued)

*Primary Examiner* — Colin T. Sakamoto
*Assistant Examiner* — Andrew W Begeman
(74) *Attorney, Agent, or Firm* — James R. Stevenson; Aaron A. Mace

(57) ABSTRACT

A method and system determine, with a computer system including one or more processors, a plurality of parameters associated with a volume in an object over time in a series of sequence blocks. In a sequence block in the series of sequence blocks, the plurality of parameters are determined as occurring simultaneously in the volume in the object. At
(Continued)

least one parameter of the plurality of parameters varies from the sequence block to another sequence block in the series of sequence blocks, and the plurality of parameters include a contrast related parameter associated with a concentration of a contrast agent in the volume in the object over time in the series of sequence blocks. The computer system generates a signal evolution based on the plurality of parameters of the volume in the object over time in the series of sequence blocks, the signal evolution defining the contrast related parameter over time in the series of sequence blocks.

18 Claims, 10 Drawing Sheets

(51) Int. Cl.
*A61B 6/00* (2006.01)
*A61M 5/00* (2006.01)
*G01R 33/54* (2006.01)
*G01R 33/56* (2006.01)

(52) U.S. Cl.
CPC ..... *G01R 33/5601* (2013.01); *G01R 33/5608* (2013.01); *G16H 30/40* (2018.01); *A61M 2205/3303* (2013.01); *A61M 2205/3379* (2013.01); *A61M 2205/50* (2013.01)

(58) Field of Classification Search
CPC ...... A61B 5/055; A61B 6/481; G01R 33/543; G01R 33/5601; G01R 33/5608
See application file for complete search history.

(56) References Cited

U.S. PATENT DOCUMENTS

| 6,385,483 | B1 | 5/2002 | Uber, III et al. |
| 6,470,889 | B1 | 10/2002 | Bae et al. |
| 6,635,030 | B1 | 10/2003 | Bae et al. |
| 6,643,537 | B1 | 11/2003 | Zatezalo et al. |
| 7,094,216 | B2 | 8/2006 | Trombley, III et al. |
| 7,556,619 | B2 | 7/2009 | Spohn et al. |
| 7,925,330 | B2 | 4/2011 | Kalafut et al. |
| 8,147,464 | B2 | 4/2012 | Spohn et al. |
| 8,295,914 | B2 | 10/2012 | Kalafut et al. |
| 8,337,456 | B2 | 12/2012 | Schriver et al. |
| 8,540,698 | B2 | 9/2013 | Spohn et al. |
| 8,723,518 | B2 | 5/2014 | Seiberlich et al. |
| 9,008,759 | B2 | 4/2015 | Kalafut et al. |
| 9,302,044 | B2 | 4/2016 | Kalafut et al. |
| 9,421,330 | B2 | 8/2016 | Kalafut et al. |
| 9,436,989 | B2 | 9/2016 | Uber, III |
| 9,618,596 | B2 | 4/2017 | Warntjes |
| 9,750,953 | B2 | 9/2017 | Kalafut |
| 9,949,704 | B2 | 4/2018 | Kalafut et al. |
| 9,959,389 | B2 | 5/2018 | Kalafut |
| 9,993,156 | B2 | 6/2018 | Warntjes |
| 2007/0078333 | A1* | 4/2007 | Abe .......... G01R 33/5601 600/420 |
| 2008/0119715 | A1* | 5/2008 | Gonzalez Molezzi .......... A61B 5/7285 600/407 |
| 2010/0030073 | A1* | 2/2010 | Kalafut ............ A61B 5/0295 600/431 |
| 2012/0235678 | A1* | 9/2012 | Seiberlich .......... G01R 33/543 324/307 |
| 2013/0211247 | A1* | 8/2013 | Kalafut ............ A61B 6/507 703/11 |
| 2019/0204402 | A1* | 7/2019 | Leporq ............ G01R 33/5601 |

FOREIGN PATENT DOCUMENTS

| JP | 5203971 B2 | 6/2013 |
| WO | 2018098130 A1 | 5/2018 |
| WO | 2018098144 A1 | 5/2018 |

OTHER PUBLICATIONS

Christen T.; et al, "MR Vascular Fingerprinting: A New Approach to Compute Cerebral Blood Volume Mean Vessel Radius, and Oxygenation Maps in the Human Brain", Neuroimage, Apr. 1, 2014, 89, 262-270.
De; Haas et al., "Rapid Simultaneous Detection of Multiple Contrast Agents Using Magnetic Resonance Fingerprinting", Proc. Intl. Soc. Mag. Reson. Med., 2016, 24; 1572, 5865-5866.
Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).
"International Preliminary Report on Patentability from PCT Application No. PCT/US2017/062768", dated Jun. 6, 2019.
Ma Dan. et al., "Magnetic resonance fingerprinting", Nature, Mar. 14, 2013, 495, 187-193.
Panda Ananya. et al., "Magnetic Resonance Fingerprinting—An Overview", Curr Opin Biomed Eng., Sep. 2017, 3, 56-66.
Pouliot Philippe; Et. Al., "Magnetic resonance fingerprinting based on realistic vasculature in mice", NeuroImage, 2017, 436, 436-445.
Schwilden; H., "A General Method for Calculating the Dosage Scheme in Linear Pharmacokinetics", Eur. J. Clin. Pharmacol., 1981, 20, 379-386.
Wilson Gregory J. et al., "Evaluation of a Tailored Injection Profile (TIP) Algorithm for Uniform Contrast-Enhanced Signal Intensity Profiles in MR Angiography", Journal of Magnetic Resonance Imaging, 2016, vol. 44 / No. 6, 1664-1672.
Lingala; et al, "Accelerated DCE MRI using constrained reconstruction based on pharmaco-kinetic model dictionaries", Proceedings of the International Society For Magnetic Resonance in Medicine, May 15, 2015, No. 196.

* cited by examiner

SYNTHETIC MAGNETIC RESONANCE IMAGING AND MAGNETIC RESONANCE FINGERPRINTING WITH A CONTRAST AGENT, AND DETERMINATION OF A CONTRAST AGENT INJECTION PROTOCOL

CROSS REFERENCE TO RELATED APPLICATIONS

This application is a 371 national phase application of International Application No. PCT/US2017/062768, filed Nov. 21, 2017, and claims the benefit of U.S. Provisional Application No. 62/425,303, filed Nov. 22, 2016, the entire disclosures of which are hereby incorporated by reference in their entirety. This application is related to International Application No. PCT/US2017/062728, filed on Nov. 21, 2017, which claims the benefit of U.S. Provisional Application No. 62/425,312, filed Nov. 22, 2016, the entire disclosure of which is hereby incorporated by reference.

BACKGROUND

Imaging techniques, such as synthetic magnetic resonance (MR) and MR fingerprinting, allow simultaneous determination of multiple MR properties or measurements of tissue and magnetic environment. These imaging techniques have potential for quantitative MR imaging and improved diagnosis and characterization of disease.

Contrast agents are used to enhance images of a region of a body obtained through imaging procedures performed with imaging technologies, such as computed tomography (CT), angiography, ultrasound, magnetic resonance imaging (MRI), nuclear medicine, molecular imaging, and/or the like. The response of healthy and diseased tissue to contrast agents is a differentiator and informer of disease and physiological state of the tissue under study. There are multiple types of contrast agents with varying properties. A blood pool contrast agent is a contrast agent that does not diffuse into tissue, but generally stays within blood vessels. An extracellular contrast agent is a contrast agent that diffuses out of the blood vessels (although generally not through the blood brain barrier), but does not diffuse into cells. There are contrast agents, such as the positron emission tomography agent fluorodeoxyglucose (FDG), which do move into cells. Magnetic resonance (MR) imaging may be performed with an injection of an MR contrast agent. Conventionally, blood pool MR contrast agents or a timeframe for image acquisition, which is insensitive to diffusion of the contrast agent out of the blood and into tissue, for example, shortly after injection or many minutes after injection when everything has effectively reached equilibrium, have been used with MR imaging. Alternatively, relatively long timeframes when diffusion has stabilized are used. In some instances, the diffusion of the contrast is intentionally imaged.

There is a need for a contrast injection system, protocol, and method which can provide in a timely fashion a desired MR contrast concentration in blood and/or in tissue such that an MR fingerprint can include one or more contrast related parameters.

SUMMARY

According to some non-limiting embodiments or aspects, provided is a method including determining, with a computer system including one or more processors, a plurality of parameters associated with a volume in an object over time in a series of sequence blocks, wherein, in a sequence block in the series of sequence blocks, the plurality of parameters are determined as occurring simultaneously in the volume in the object, wherein at least one parameter of the plurality of parameters varies from the sequence block to another sequence block in the series of sequence blocks, and wherein the plurality of parameters include at least one contrast related parameter associated with a concentration of a contrast agent in the volume in the object over time in the series of sequence blocks; and generating, with the computer system, a signal evolution based on the plurality of parameters of the volume in the object over time in the series of sequence blocks, wherein the signal evolution defines the at least one contrast related parameter over time in the series of sequence blocks.

According to some non-limiting embodiments or aspects, provided is a computing system including one or more processors programmed or configured to determine a plurality of parameters associated with a volume in an object over time in a series of sequence blocks, wherein, in a sequence block in the series of sequence blocks, the plurality of parameters are determined as occurring simultaneously in the volume in the object, wherein at least one parameter of the plurality of parameters varies from the sequence block to another sequence block in the series of sequence blocks, and wherein the plurality of parameters include at least one contrast related parameter associated with a concentration of a contrast agent in the volume in the object over time in the series of sequence blocks; and generate a signal evolution based on the plurality of parameters of the volume in the object over time in the series of sequence blocks, wherein the signal evolution defines the at least one contrast related parameter over time in the series of sequence blocks.

Further non-limiting embodiments or aspects are set forth in the following numbered clauses:

Clause 1. A method comprising: determining, with a computer system comprising one or more processors, a plurality of parameters associated with a volume in an object over time in a series of sequence blocks, wherein, in a sequence block in the series of sequence blocks, the plurality of parameters are determined as occurring simultaneously in the volume in the object, wherein at least one parameter of the plurality of parameters varies from the sequence block to another sequence block in the series of sequence blocks, and wherein the plurality of parameters include at least one contrast related parameter associated with a concentration of a contrast agent in the volume in the object over time in the series of sequence blocks; and generating, with the computer system, a signal evolution based on the plurality of parameters of the volume in the object over time in the series of sequence blocks, wherein the signal evolution defines the at least one contrast related parameter over time in the series of sequence blocks.

Clause 2. The method of clause 1, wherein determining the plurality of parameters associated with the volume in the object over time in the series of sequence blocks is based on a model associated with one or more resonant species in the volume in the object, wherein the model simulates behavior of the one or more resonant species in the volume in the object in response to magnetic resonance (MR) excitation in the series of sequence blocks.

Clause 3. The method of any of clauses 1 and 2, further comprising: determining the at least one contrast related parameter based on data associated with the concentration of the contrast agent in blood associated with the volume over time in the series of sequence blocks.

Clause 4. The method of any of clauses 1-3, further comprising: determining the at least one contrast related parameter based on data associated with a fraction of the volume including the blood over time in the series of sequence blocks.

Clause 5. The method of any of clauses 1-4, further comprising: determining the at least one contrast related parameter based on data associated with a concentration of the contrast agent in an extracellular volume of the object over time in the series of sequence blocks and data associated with a fraction of the volume in the object including the extracellular volume over time in the series of sequence blocks.

Clause 6. The method of any of clauses 1-5, wherein the at least one contrast related parameter is substantially constant over time in the series of sequence blocks.

Clause 7. The method of any of clauses 1-6, wherein the at least one contrast related parameter changes at a substantially linear rate over time in the series of sequence blocks.

Clause 8 The method of any of clauses 1-7, wherein the at least one contrast related parameter is substantially constant during the sequence block.

Clause 9. The method of any of clauses 1-8, wherein the at least one contrast related parameter increases at a substantially linear rate over a first subset of sequence blocks in the series of sequence blocks.

Clause 10. The method of any of clauses 1-9, wherein the at least one contrast related parameter decreases at a substantially linear rate over a second subset of sequence blocks in the series of sequence blocks.

Clause 11. The method of any of clauses 1-10, wherein the signal evolution defines the at least one contrast related parameter as a linear function.

Clause 12. The method of any of clauses 1-11, further comprising: determining, with a computer system comprising one or more processors, an input function for the volume in the object based on data associated with the object, the input function for the volume providing a time enhancement output for a given input; determining, with the computer system, a desired time enhancement output associated with the at least one contrast related parameter; and using the input function for the volume to determine, with the computer system, the signal evolution defining the at least one contrast related parameter over time in the series of sequence blocks.

Clause 13. The method of any of clauses 1-12, further comprising: storing, with the computer system, the signal evolution in association with the volume in the object in a database.

Clause 14. The method of any of clauses 1-13 further comprising: receiving, with the computer system, another signal evolution; comparing, with the computer system, the another signal evolution to the signal evolution stored in the database; and determining, based on the comparison, one or more resonant species associated with the another signal evolution.

Clause 15. The method of any of clauses 1-14, further comprising: controlling, with the computer system, a nuclear magnetic resonance (NMR) apparatus to apply radio frequency (RF) energy to another volume in another object in another series of sequence blocks to expose the another volume to the MR excitation in the another series of sequence blocks, wherein the MR excitation in each sequence block in the another series of sequence blocks causes the one or more resonant species in the another volume to simultaneously produce individual signals in that sequence block, controlling, with the computer system, the NMR apparatus to acquire the simultaneously produced individual signals in each sequence block in the another series of sequence blocks; and determining, with the computer system, the another signal evolution based on the simultaneously produced individual signals acquired from each sequence block.

Clause 16. The method of any of clauses 1-15, further comprising: determining, with a computer system comprising one or more processors, an input function for a patient based on data associated with the patient, the input function for the patient providing a time enhancement output for a given input; determining, with the computer system, a desired time enhancement output based on the at least one contrast related parameter; using the input function for the patient to determine, with the computer system, an injection protocol input, wherein the injection protocol input is derived based on a time to achieve the desired time enhancement output; and controlling, with the computer system, an injector to deliver the contrast agent based on the determined injection protocol input.

Clause 17. The method of any of clauses 1-16, wherein the injection protocol input is optimized to minimize a time to achieve the desired time enhancement output.

Clause 18. The method of any of clauses 1-17, wherein the desired time enhancement output is associated with the concentration the contrast agent in a blood pool of the patient over time.

Clause 19. A computing system comprising: one or more processors programmed or configured to: determine a plurality of parameters associated with a volume in an object over time in a series of sequence blocks, wherein, in a sequence block in the series of sequence blocks, the plurality of parameters are determined as occurring simultaneously in the volume in the object, wherein at least one parameter of the plurality of parameters varies from the sequence block to another sequence block in the series of sequence blocks, and wherein the plurality of parameters include at least one contrast related parameter associated with a concentration of a contrast agent in the volume in the object over time in the series of sequence blocks; and generate a signal evolution based on the plurality of parameters of the volume in the object over time in the series of sequence blocks, wherein the signal evolution defines the at least one contrast related parameter over time in the series of sequence blocks.

Clause 20. The computing system of clause 20, wherein the one or more processors are further programmed or configured to: determine an input function for the volume in the object based on data associated with the object, the input function for the volume providing a time enhancement output for a given input; determine a desired time enhancement output associated with the at least one contrast related parameter; and use the input function for the volume to determine the signal evolution defining the at least one contrast related parameter over time in the series of sequence blocks.

Clause 21. The computing system of any of clauses 20 and 21, wherein the one or more processors are further programmed or configured to: determine an input function for a patient based on data associated with the patient, the input function for the patient providing a time enhancement output for a given input; determine a desired time enhancement output based on the at least one contrast related parameter; use the input function for the patient to determine an injection protocol input, wherein the injection protocol input is derived based on a time to achieve the desired time enhancement output; and control an injector to deliver the contrast agent based on the determined injection protocol input.

DETAILED DESCRIPTION

Figure 1:
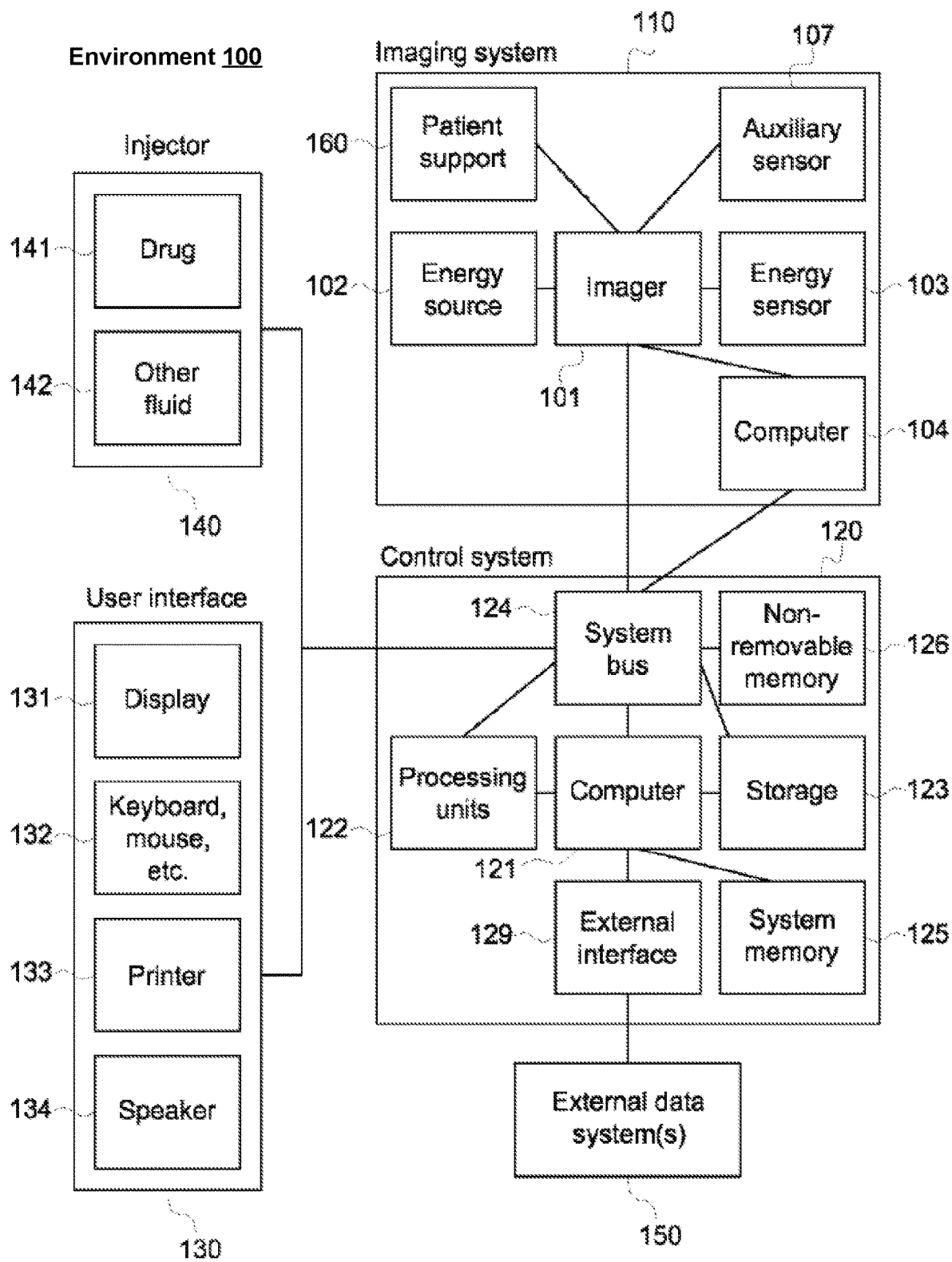
FIG. 1 is a schematic diagram of a non-limiting embodiment or aspect of an environment in which systems and/or methods, described herein, can be implemented.

The following detailed description of non-limiting embodiments refers to the accompanying drawings. The same reference numbers in different drawings may identify the same or similar elements.

As explained in "Overview of Magnetic Resonance Fingerprinting by Vikas Gulani et al., MAGNETOM Flash (65), February 2016, which is incorporated herein by reference in its entirety, a magnetic resonance (MR) fingerprinting technique aims at providing simultaneous, quantitative measurements of multiple parameters such as T1, T2, relative spin density, $B_0$ inhomogeneity (off-resonance frequency), etc., using a single, time-efficient acquisition. MR fingerprinting changes the way quantitative MRI is performed with a different approach from that of conventional techniques. Instead of performing an acquisition with all but one sequence parameter constant, MR fingerprinting deliberately varies acquisition parameters in a pseudorandom fashion such that each tissue generates a unique signal evolution. It is possible to simulate signal evolutions from first principles using different physical models for a wide variety of tissue parameter combinations, which are collected together in a database called a dictionary or library. After the acquisition, a pattern recognition algorithm is used to find the dictionary or library entry that best represents the acquired signal evolution of each voxel. The parameters that were used to simulate the resulting best match are assigned to the voxel. This process is analogous to the fingerprinting identification process used by forensic experts to identify persons of interest, The acquired signal evolution is unique for each tissue and can be seen as the collected fingerprint that has to be identified. The dictionary or library is similar to the database where all the known fingerprints are stored, together with the information relative to each person. In the forensic case example, each fingerprint points to the feature identification of the associated person such as name, height, weight, eye color, date of birth, etc. Similarly, in the case of MR fingerprinting, each fingerprint in the dictionary points to the MR related identification features of the associated tissue such as T1, T2, relative spin density, $B_0$, diffusion, etc. After the acquisition, the fingerprint contained in a voxel is compared with all the entries in the dictionary or library. The dictionary or library entry that best matches the acquired fingerprint is considered a positive match, meaning that the tissue represented in the voxel has been identified, All the known parameters relative to that fingerprint can be retrieved from the dictionary or library and assigned to the voxel. The uniqueness of the different signal components and the accuracy with which the dictionary or library is simulated are two crucial components for the correct estimation of the tissue parameters.

As further explained by Gulani et al., if a TrueFISP pulse sequence is used, dimensions or variables that the dictionary or library may contain include T1 values form 100 to 2000 ms in 20 ms steps and 2000 to 5000 ms in 300 ms steps, T2 values from 20 to 100 ms in 5 ms steps, 100 to 200 ms in 10 ms steps, and 200 to 1900 ms in 200 ms steps, and off-resonance values from −250 to −190 kHz in 20 kHz steps, −50 to +50 kHz in 1 kHz steps, and +190 to +250 kHz in 20 kHz steps.

In the work described in "MR Vascular Fingerprinting: A New Approach to Compute Cerebral Blood Volume, Mean Vessel Radius, and Oxygenation Maps in the Human Brain" by G. Zaharchuk et al., published as Neuroimage, 2014 April 1; 89: 262-270, which is incorporated by reference in its entirety herein, a blood pool contrast agent is used. For example, a dictionary corresponding to an MR signal prior to injection is identical for all volunteers, but the dictionary of the MR signals after injection is simulated individually for each volunteer with the magnetic susceptibility increase due to the contrast agent injection. The concentration of the contrast agent is estimated based upon a weight of the patient and is a fixed input into the computation of the dictionary. However, the concentration of the contrast agent is not a variable fit or extracted via the MR fingerprinting process. It is a single value that is used to compute all the signal evolutions or fingerprints to put into the dictionary or library.

It is a goal of the present disclosure to provide a system and a method, optionally including an injection system and protocol, which enables inclusion of at least one contrast related parameter in a dictionary or library of parameters to be fit. In some non-limiting embodiments, a calculated or generated signal evolution includes the effect of one or more contrast related parameters at two or more values. Thus, when a match occurs with a known signal evolution in the dictionary or library, the contrast related parameter for that voxel is thereby known or determined.

In some non-limiting embodiments, imaging techniques, such as synthetic magnetic resonance (MR) and MR fingerprinting, apply a series of different or varying pulse sequences to a volume (e.g., a voxel) in an object (e.g., a patient) and use analytical analysis of signals produced therefrom to determine properties and/or parameters of the volume in the object. For example, MR fingerprinting employs a series of varied sequence blocks that produce different signal evolutions in different resonant species (e.g., water, fat, bone, tissues, etc.) to which RF energy is applied. As an example, RF energy applied in a sequence block to a volume including different individual resonant species causes the different individual resonant species to simultaneously produce different individual nuclear magnetic resonance (NMR) signals. Signals can be collected over the series of varying sequence blocks to identify a signal evolution of the volume, and resonant species in the volume can be characterized by comparing the signal evolution to known signal evolutions in a pattern matching process. As more parameters of the sequence blocks (e.g., flip angle, echo time, RF amplitude, etc.) are varied, a potentially richer signal is retrieved with greater information content that facilitates producing more distinct and, thus, more matchable signal evolutions.

However, these types of imaging techniques generally do not use contrast agents, and those that do assume a constant concentration of contrast agent over the scan sequence and, thus, a static effect on parameters, such as T1, T2, and/or the like. For example, the MR fingerprinting dictionary or library does not contain a contrast agent related parameter, and imaging processes and analyses for MR fingerprinting do not consider or model parameters associated with a contrast agent (e.g., contrast agent concentration, etc.) in a dictionary or library, for example, as a variance between sequence blocks and/or to model signal evolutions. In this way, these types of imaging techniques may not be as effective in producing and analyzing signals for assessing and differentiating between tissues, benign and malignant tumors, vascular properties, diseases, and/or the like.

As disclosed herein, in some non-limiting embodiments, a computer system including one or more processors determines a plurality of parameters associated with a volume in an object over time in a series of sequence blocks, wherein, in a sequence block in the series of sequence blocks, the plurality of parameters are determined as occurring simultaneously in the volume in the object. At least one parameter of the plurality of parameters varies from the sequence block to another sequence block in the series of sequence blocks, and the plurality of parameters include a contrast related parameter associated with a concentration of a contrast agent in the volume in the object over time in the series of sequence blocks. The computer system generates a signal evolution based on the plurality of parameters of the volume in the object over time in the series of sequence blocks, the signal evolution defining the contrast related parameter over time in the series of sequence blocks. In this way, the computer system generates a signal evolution associated with the concentration of the contrast agent in the volume in the series of sequence blocks. Accordingly, the computer system enables more effective production and analysis of signals for assessing and/or differentiating between tissues, benign and malignant tumors, vascular properties, diseases, and/or the like.

In some non-limiting embodiments, increasing a number of parameters and/or a complexity of a parameter in a parameter modeling process associated with these types of imaging techniques can significantly increase an amount of processing time and software and/or hardware resources required to produce and analyze the signal evolutions. In this way, use of unconstrained, time varying parameters makes a process of analyzing the signals (e.g., determining and/or generating a signal evolution, convergence in the pattern matching process, etc.) less constrained and, thus, processing more difficult and time-consuming. As an example, a response of some parameters is a non-linear function of contrast agent concentration, and an arbitrary, unconstrained parameter that changes over time makes processes associated with that parameter less constrained.

As disclosed herein, in some non-limiting embodiments, the contrast related parameter is substantially linear over time (e.g., substantially constant over time in the series of sequence blocks, changes at a substantially linear rate over time in the series of sequence blocks, etc.). For example, the contrast related parameter associated with the concentration of a contrast agent in the volume can be associated with a substantially linear concentration of the contrast agent in the blood over time in the series of sequence blocks and/or an injector can be controlled to deliver the contrast agent to provide the substantially linear concentration of the contrast agent in the blood over time in the series of sequence blocks. In this way, the contrast related parameter is substantially constant over time in the series of sequence blocks and/or changes at a substantially linear rate over time in the series of sequence blocks. Accordingly, a process of analyzing the signals (e.g., determining and/or generating a signal evolution, convergence in the pattern matching process, etc.) is more constrained and, thus, an amount of processing time and software and/or hardware resources required to produce and analyze the signals is decreased.

In some non-limiting embodiments, it is preferable to start an imaging procedure after a contrast agent is uniformly distributed (e.g., at a steady or linearly changing state) in the blood associated with the volume in the object (e.g., in the blood pool of the patient). Moreover, it may be preferable to start an imaging procedure as soon as possible after delivery of a contrast agent, as well as to reduce a time associated with delivery of the contrast agent and/or performance of the imaging procedure. For example, by starting an imaging procedure as soon as possible after delivery of a contrast agent (and/or by reducing preparation and/or delivery time), efficiency of medical imaging equipment use can be improved and procedures that image before and after distribution of the contrast can be performed. As an example, a patient lying in an imaging scanner waiting for a contrast agent to distribute is a waste of scanner time and an inconvenience to the patient and a technologist performing the scan.

However, processes for delivering a contrast agent may follow injection protocols that delay a time until a contrast agent is uniformly distributed in the blood pool in order to provide relatively long time periods (e.g., many minutes) associated with the uniform distribution and/or follow injection protocols that provide a relatively uniform high contrast level for a relatively short period of time (e.g., 30 seconds), which results in decay after the delivery is stopped and overshoot of a desired uniform blood pool level.

As disclosed herein, in some non-limiting embodiments, the computer system determines an input function (e.g., a blood pool input function) for a patient based on data associated with the patient, the input function providing a time enhancement output for a given input. The computer system determines a desired time enhancement output based on the contrast related parameter and uses the input function for the patient to determine an injection protocol input that is derived based on a time to achieve the desired time enhancement output. The computer system controls an injector to deliver the contrast agent based on the determined injection protocol input. In this way, the contrast agent can be delivered in a manner that is customized for individual patients and reduces or minimizes a time to achieve a desired concentration of the contrast parameter in the blood pool of the patient and/or in the volume in the object over time in the series of sequence blocks, without being delayed in reaching, and/or overshooting, a desired uniform blood pool level. Accordingly, an imaging procedure can begin sooner after a contrast agent is appropriately distributed in the blood pool of a patient (e.g., as soon as possible after injection of a contrast agent), and a shorter injection time for delivery of the contrast agent and/or a reduction in a total imaging time can be achieved. Moreover, more customized injections enable more standardized images for more efficient and accurate data analysis and more efficient use of contrast agents.

Referring now to FIG. 1, FIG. 1 is a diagram of a non-limiting embodiment or aspect of an environment 100 in which systems and/or methods, described herein, can be implemented. As shown in FIG. 1, environment 100 includes imaging system 110, control system 120, user interface 130, injector 140, and/or external data system(s) 150. In some non-limiting embodiments, imaging system 110, control system 120, user interface 130, injector 140, and/or external data system(s) 150 include one or more devices capable of receiving a plurality of signals from a volume (e.g., a voxel) in an object (e.g., a patient) exposed to magnetic resonance (MR) excitation in a series of sequence blocks and generating information associated with a concentration of a contrast agent in the volume based on the plurality of signals. For example, imaging system 110, control system 120, user interface 130, injector 140, and/or external data system(s) 150 include one or more devices capable of delivering the contrast agent to the patient (and/or determining an injection protocol for delivering the contrast agent to the patient), exposing the volume in the patient to the MR excitation in a synthetic MR imaging process and/or a MR fingerprinting imaging process, acquiring the plurality of signals from the volume in the synthetic MR and/or MR fingerprinting imaging processes, and generating the information associated with the concentration of the contrast agent in the volume based on the plurality of signals.

In some non-limiting embodiments, imaging system 110, control system 120, user interface 130, injector 140, and/or external data system(s) 150 include one or more devices capable of determining an input function (e.g., a blood pool input function) for a patient based on data associated with the patient, the input function providing a time enhancement output for a given input, determining a desired time enhancement output, using the input function to determine an injection protocol input, and controlling an injector to deliver the contrast agent based on the determined injection protocol input. In some non-limiting embodiments, the injection protocol input is derived based on (and/or optimized to minimize) a time to achieve at least one of (i) a substantially constant concentration of a contrast agent in the blood pool of the patient over time and (ii) a substantially linear rate of change in the concentration of the contrast agent in the blood pool of the patient over time.

In some non-limiting embodiments, imaging system 110 is configured to image a patient and includes imager 101 including energy source 102 configured to transmit energy into a patient and energy sensor 103 configured to collect energy from the patient and convert energy received over time into a stream of signals and/or data that can be transferred to and collected by control system 120, and/or computer 104 associated and/or integrated with imaging system 110, that is capable of interpreting and manipulating the signals and/or data and displaying an image on display 131 associated with user interface 130. The energy can be transmitted through the patient or reflected, scattered, or otherwise interact with the patient or a drug (e.g., a contrast agent) given to the patient. Sensor 103 associated with imaging system 110 can be positioned to receive either transmitted or reflected/scattered energy and use the received energy to produce data that can be used to produce an image of the patient. Energy source 102 may generally be an integral part of imaging system 110; however, in some non-limiting embodiments, energy source 102 is the patient himself in, for example, black body radiation. In some non-limiting embodiments, energy source 102 is a drug, tracer, and/or contrast fluid 141 including a contrast agent which contains a radioactive atom. In some non-limiting embodiments, imaging system 110 includes positron emission tomography (PET) imagers, computed tomography (CT) imagers, magnetic resonance imaging (MR) imagers, single-photon emission computed tomography (SPECT) imagers, and/or combinations thereof including, for example, PET/CT imagers, PET/MR imagers, SPECT/CT imagers, and/or the like.

In some non-limiting embodiments, the signals, data and/or information acquired by imaging system 110 can be transmitted to control system 120 that can include various components necessary to compile data acquired from imager 101, analyze the data, and transmit the data to an output device in a user accessible format. Control system 120 may include one or more computers 121 or similar computing devices having a computer-readable storage medium 123 capable of storing computer-readable program code or instructions that cause processing unit 122 to execute, configure, or otherwise implement methods, processes, and transformational data manipulations necessary to carry out methods described herein. Computer 121 can include one or more processing units 122 (typically referred to as a central processing unit or CPU) that serve to execute computer-based instructions received in the appropriate data form and format. In some non-limiting embodiments, processing unit 122 can be in the form of multiple processors executing code in series, in parallel, or in any other manner for appropriate implementation of the computer-based instructions. In some non-limiting embodiments, computer 121 may be operably configured to execute appropriate software to perform and implement the processing steps of the methods described above. Computer 121 may be in the form of a personal computer coupled one or more other components in environment 100, a processor formed integrally with imaging system 110, a computer separate from imaging system 110, or any other type of computing device having the necessary processing hardware and/or software to appropriately process data to effectively implement the methods and systems described herein.

In some non-limiting embodiments, control system 120 includes system bus 124 to facilitate appropriate data communication and processing information between various components of computer 121. System bus 124 may be any of several types of bus structures, including a memory bus or memory controller, a peripheral bus, or a local bus using any of a variety of bus architectures. In some non-limiting embodiments, system bus 124 may facilitate data and information communication between various components (whether internal or external to computer 121) through interfaces.

In some non-limiting embodiments, computer 121 includes one or more discrete computer-readable media components that can be contained on computer-readable storage medium 123. Computer-readable storage medium 123 may be any method or technology for storage of information such as computer-readable instructions, data structures, program modules, or other data, including, but not limited to, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by computer 121. The computer-readable media contained on computer readable storage medium 123 may include any media that can be accessed by computer 121, such as volatile media, non-volatile media, removable media, non-removable media, and the like. In some non-limiting embodiments, the computer-readable media may include communications media, such as computer-readable instructions, data structures, program modules, or other data in a modulated data signal such as a carrier wave, or other transport mechanism. In some non-limiting embodiments, the computer-readable media may include any information delivery media, wired media (such as a wired network and a direct-wired connection), and wireless media (such as acoustic signals, radio frequency signals, optical signals, infrared signals, biometric signals, bar code signals, etc.). Combinations of any of the above are also included within the scope of computer-readable media.

In some non-limiting embodiments, computer 121 further includes system memory 125 such as volatile and non-volatile memory, ROM, and/or RAM. A basic input/output system (BIOS) with appropriate computer-based routines assists in transferring information between components within computer 121 and can be stored in ROM. The RAM portion of system memory 125 typically contains data and program modules that are immediately accessible to or presently being operated on by processing unit 122 such as, for example, an operating system, application programming interfaces, application programs, program modules, program data, and other instruction-based computer-readable code.

In some non-limiting embodiments, computer 121 includes other removable or non-removable, volatile or non-volatile computer storage media products. For example, computer 121 includes non-removable memory 126 that includes a non-removable, non-volatile magnetic medium, a removable, non-volatile memory interface that communicates with and controls a magnetic disk drive unit that reads from and writes to a removable, non-volatile magnetic disk, an optical disk drive unit that reads from and writes to a removable, non-volatile optical disk, such as a CD ROM, a Universal Serial Bus (USB) port for use in connection with, for example, a removable memory card, and the like and combinations thereof. Other removable or non-removable, volatile or non-volatile computer storage media can be used in exemplary control system 120, including, but not limited to, magnetic tape cassettes, DVDs, digital video tape, solid state RAM, solid state ROM, and the like. These removable or non-removable, volatile or non-volatile magnetic media can be configured to be in communication with the at least one processing unit 122 and other components of computer 121 via system bus 124. The drives and their associated computer storage media discussed above provide storage of operating systems, computer-readable instructions, application programs, data structures, program modules, program data, and other instruction-based computer-readable code for computer 121 whether duplicative or not of the information and data in system memory 125.

In some non-limiting embodiments, environment 100 includes one or more user interfaces 130 associated with control system 120. For example, user interface 130 includes one or more displays 131 or graphical user interfaces (GUI) that are capable of displaying images and other graphics in color or black and white and configured to present or provide data and information to an operator in an intelligible form or format. In some non-limiting embodiments, display 131 may be configured to allow a user to program or otherwise operate one or more components in environment 100, and display 131 may display real-time data with regard to the operation of the one or more components. For example, in some non-limiting embodiments, display 131 has touch-screen capabilities or is otherwise configured to allow a user to interact with control system 120 and, for example, computer 121 associated with control system 120, by manipulating or touching display 131. In some non-limiting embodiments, user interface 130 may include a keyboard, mouse, or other device 132 configured to allow the user to program or otherwise operate one or more components in environment 100.

In some non-limiting embodiments, display 131 may be included as part of a laptop or tablet computer that is electronically associated with one or more components in environment 100 by a hard wired and/or wireless network. In some non-limiting embodiments, display 131 may be fixed to and/or integrated with imaging system 110, control system 120, and/or injector 140 via a housing that encompasses imaging system 110, control system 120, and/or injector 140. Display 131 may be configured to be tilted or swiveled to allow display 131 to be positioned by an operator. In some non-limiting embodiments, display 131 is positioned remote from the imaging system 110, control system 120, and/or injector 140 and attached to the imaging system 110, control system 120, and/or injector 140 by a hard wired and/or wireless network.

In some non-limiting embodiments, user interface 130 includes a printer 133 that is configured to physically display this information and data in print form. Printer 133 may be of any type and includes off the shelf ink-jet and laser printers, In some non-limiting embodiments, printer 133 may be configured to print adhesive backed labels. In some non-limiting embodiments, user interface 130 includes speaker 134 to audibly present this information and data in audible form. For example, speaker 134 may be configured to produce an audible "beep" when the method or a portion of the method is complete. For example, speaker 134 may be configured to provide a "beep" when maximum blood volume has been reached or when the input function has reached upper or lower thresholds, In various embodiments, such devices may be in communication with the computer or other control system through output interfaces.

In some non-limiting embodiments, environment 100 is configured to allow a user to enter commands, information, and data into the computer 121 using the touch-screen of GUI display 131 via user interface 130. However, it has been envisioned that an operator may enter commands, information, and data into computer 121 using other attachable or operable input devices, such as a keyboard, a mouse, a remote control device, a microphone, a trackball, a joystick, a touchpad, a scanner, a tablet computer, and the like, via user interface 130. Any arrangement that facilitates the input of data and information to computer 121 (and/or computer 104) from an outside source may be used including, for example, hard wiring or accessing using a wireless network device, such as Bluetooth, a wireless internet connection, or a cellular connection. As discussed, these and other input devices are often connected to control system 120 through user interface 130 coupled to system bus 124, but may be connected by other interface and bus structures, such as a parallel port, game port, or a USB.

In some non-limiting embodiments, display 131 provides output images that are single plane representations of a 3D voxel data set or 3D graphical images. In some non-limiting embodiments, the output image may provide all the data presented to the user. In some non-limiting embodiments, the output image may further provide various physiologically relevant parameters such as blood volume, blood flow, drug uptake or diffusion, drug metabolism that can provide information to the user that can be used, for example, in diagnosis of a patient's condition.

In some non-limiting embodiments, control system 120 includes external interface 129 for communications of data into and/or out of environment 100. External interface 129 can connect to one or more other external data or computer systems 150 over any of a multitude of communications medium with their applicable communications protocols. The data coming in may include, for example, patient and procedure or protocol ordering or schedule information. Data going out can include DICOM data going to a PACS system, or information about the procedure to a hospital information systems (HIS) or radiology information system (RIS). Such information can be used for billing, safety, efficiency or a myriad of other uses.

In some non-limiting embodiments, computer 104, control system 120, and/or external data system(s) 150 provide, access, and/or store in a library or database signal evolutions associated with relevant combinations of resonant species that may be acquired and available to an imaging system (e.g., an NMR fingerprinting imaging system). The library or database may include known signals that may be referred to as baseline signatures or known signal evolutions. In some non-limiting embodiments, the library may include simulated and/or predicted signal evolutions. For example, "known" signal evolutions may include previously acquired signal evolutions and/or simulated signal evolutions.

In some non-limiting embodiments, computer 104 and/or computer 121 include a protocol simulator that is configured to simulate delivering a contrast agent, collecting the data, and analyzing the data. During simulation, patient circulation, uptake of the contrast agent by selected tissues, and excretion and degradation of the contrast agent can be simulated. The compartmental model operates within a physical 3D or 4D model of the body, so that tissue concentrations can be given a location in space. Such models have been developed for CT, PET, and SPECT image acquisition. These models allow iterative reconstruction methods to account for various sources of noise and distortion. Using the model with the known capabilities and limitations of imaging system 110, the simulator creates the data that would have been measured by the real imaging system 110 given the simulated distribution of the contrast agent. This data is then used by control system 120, and a quantitative assessment and diagnosis can be made. Because the quantitative results come from a simulation, the results can be compared to the compartmental model parameter that went into the simulations to assess how well the proposed protocol would allow for identification of the correct compartmental properties. This simulator may not be used for every patient but can be used to assess and optimize imaging and drug delivery protocols for new drugs, new theories of disease, or when there is a significant deviation in some condition, such as patient weight, size, or another factor.

In some non-limiting embodiments, the protocol simulator simulates and/or estimates data associated with the volume in the series of sequence blocks. For example, the protocol simulator simulates or estimates data associated with at least one of the following: a concentration of a contrast agent in a volume in an object in a sequence block in the series of sequence blocks, the concentration of the contrast agent in the volume over time in the series of sequence blocks, the concentration of the contrast agent in the blood pool of the patient in the sequence block, the concentration of the contrast agent in the blood pool of the patient over time in the series of sequence blocks, a fraction of the volume in the object including the blood in the sequence block, the fraction of the volume in the object including the blood over time in the series of sequence blocks, the concentration of the contrast agent in an extracellular volume of the object, a fraction of the volume in the object including the extracellular volume in the sequence block, the concentration of the contrast agent in the extracellular volume of the object and the fraction of the volume in the object including the extracellular volume over time in the series of sequence blocks, and/or the like.

In some non-limiting embodiments, a physician or other medical personnel carry out injection or delivery of a contrast agent manually. In some non-limiting embodiments, environment 100 includes injector 140 configured to inject, deliver, or administer contrast fluid 141 including a contrast agent to a patient, and in some non-limiting embodiments, injector 140 can be further configured to inject or administer saline or other fluid 142 to a patient before, during, or after administration of contrast fluid 141. For example, injector 140 can simply inject one or more prescribed dosages of contrast fluid 141 directly into a patient's blood stream via a hypodermic needle and syringe. In some non-limiting embodiments, injector 140 is configured to continually administer saline 142 to a patient through a peripheral IV line (Ply) and one or more prescribed dosages of contrast fluid 141 may be introduced into PIV and administered to the patient. In some non-limiting embodiments, injector 140 may be configured to inject a dose of contrast fluid 141 followed by administration of a particular volume of saline 142.

In some non-limiting embodiments, injector 140 may be configured to administer a single contrast agent. In some non-limiting embodiments injector 140 may be configured to deliver two or more different contrast agents. In implementations in which the system is configured to deliver multiple contrast agents, injector 140 may allow the operator to switch configurations depending on the intended procedure. The amount of each contrast agent delivered by the system may vary among embodiments and based on the protocol being used. Generally, a physician or other qualified medical personnel can determine an appropriate amount of contrast agent to be delivered to a particular patient using metrics regarding the patient as described herein. Because of the flexibility of the system, any amount of one or more contrast agents can be delivered. Injector 140 may be configured to inject two or more contrast agents either individually, sequentially, or simultaneously. As such, in some non-limiting embodiments, injector 140 includes two or more reservoirs such as vials or syringes capable of holding a radiopharmaceutical prior to administration. Injector 140 may further include additional medical fluid reservoirs capable of holding, for example, saline, other drugs, or other fluids.

Exemplary injection systems are those that are disclosed in: U.S. patent application Ser. No. 09/715,330, filed on Nov. 17, 2000, issued as U.S. Pat. No. 6,643,537; U.S. patent application Ser. No. 09/982,518, filed on Oct. 18, 2001, issued as U.S. Pat. No. 7,094,216; U.S. patent application Ser. No. 10/825,866, filed on Apr. 16, 2004, issued as U.S. Pat. No. 7,556,619; U.S. patent application Ser. No. 12/437,011, filed May 7, 2009, issued as U.S. Pat. No. 8,337,456; U.S. patent application Ser. No. 12/476,513, filed Jun. 2, 2009, issued as U.S. Pat. No. 8,147,464; and U.S. patent application Ser. No. 11/004,670, filed on Dec. 3, 2004, issued as U.S. Pat. No. 8,540,698, the disclosures of each of which are incorporated herein by reference in their entireties.

Environment 100 may be configured to deliver any contrast agent. In some non-limiting embodiments, the contrast agent includes a blood pool agent (e.g., ferumoxytol) that stays in the blood vessels and does not diffuse into the extravascular or intracellular spaces. In some non-limiting embodiments, the contrast agent includes a diffusible contrast agent (e.g., gadolinium) that diffuses into the extravascular or intracellular spaces. For example, injector 140 may be configured to deliver any radiopharmaceutical known in the art alone or in combination with other pharmaceutical compositions.

In some non-limiting embodiments, injector 140, in combination with control system 120, enables operation and synchronization of administration of contrast agent for short events such as a seizure or a CT scan or longer events such as sustained levels of neurotransmitter for a brain study or other long time constant PK studies. Control system 120 can provide patient specific injection protocols to achieve desired blood, plasma, and/or tissue levels of contrast agent. Injector 140 can provide a short tight bolus injection of contrast fluid 141 including the contrast agent with or without saline or other fluid 142 flush for first pass or dynamic visualization of perfusion differences. In some non-limiting embodiments, injector 140 provides slow injection of contrast agent 141. For example, control system 120 enables the user to program injector 140 to inject contrast fluid 141 including the contrast agent at a certain rate based on volume (ml), mass (mg), or activity (mCi) over time. Therefore, injection of, for example, a 30 ml dose of a radiopharmaceutical having an activity of 10 mCi can be carried out over, for example, 10 seconds, 20 seconds, 30 seconds, 45 seconds, 60 seconds, 90 seconds, 1 minute, 2 minutes, 3 minutes, 5 minutes, 10 minutes, 20 minutes, 30 minutes, 1 hour, or the so forth and any time period selected by the operator or user. In some non-limiting embodiments, control system 120 enables the user to program injector 140 to inject several discrete doses of contrast fluid 141 including the contrast agent over a period of time, for example, one 10 ml injection every 5 minutes or 10 minutes for 30 minutes or 40 minutes. In some non-limiting embodiments, control system 120 can control injector 140 to vary the injection based upon feedback about the condition of the patient and/or based upon the measurements of energy sensor 103 and/or auxiliary sensor 107 associated with imaging system 110. For example, a certain dose of contrast fluid 141 including the contrast agent can be administered when an input function reaches a particular threshold, or injection can be halted when an adverse event is observed or detected.

In some non-limiting embodiments, environment 100 includes auxiliary sensors 107 that track and monitor additional patient body functions during an imaging procedure. Such auxiliary sensors 107 are not limited and can include electro-cardio grams (ECG), respiration monitors, motion sensors, and the like and combinations thereof. In some non-limiting embodiments, auxiliary sensors 107 are configured to continuously monitor, for example, respiration, ECG, EEG, and/or other physiological indications of the physical state or status of the patient that can affect how the data collected is adjusted, as well as to directly measure concentration of a contrast agent in the blood pool or another volume of an object in the patient. For example, respiration moves the organs of the chest and abdomen in a repeatable way. ECG is synchronized with changes in heart wall position and wall thickness, which can affect the correct measurement of the image derived input function. In addition, motion correction or compensation is useful in the more accurate analysis of any voxel properties. Data acquired by auxiliary sensors 107 can be acquired in real time by imaging system 110 and collected and/or processed by control system 120 and incorporated into output provided to the user through the user interface 130.

In some non-limiting embodiments, environment 100 includes one or more patient supports or patient positioners 160 for maintaining patients in a constant known position during the scan. Normally no restraint is applied to the patient in PET imaging because dynamic scans are not routinely done in most clinical practices. Sometimes straps are used to make sure that the patient does not fall off of the imaging table or platform so that the patient feels secure. In some non-limiting embodiments, sealed bags of polystyrene beads may be provided on the table or platform on which the patient lays that move and conform to the contours of the patient when at atmospheric pressure. When the air is removed from the bag, it becomes a relatively rigid brace thereby providing support for the patient while preventing or reducing patient motion. In some non-limiting embodiments, patient support 160 can quickly and accurately move the patient between scan or bed positions as the scan takes place ensuring that events detected by energy sensor 103 are attributed to the correct voxel by system controller 120 during analysis.

The number and arrangement of systems, devices, and networks shown in FIG. 1 are provided as an example. There can be additional systems, devices and/or networks, fewer systems, devices, and/or networks, different systems, devices and/or networks, or differently arranged systems, devices, and/or networks than those shown in FIG. 1. Furthermore, two or more systems or devices shown in FIG. 1 can be implemented within a single system or a single device, or a single system or a single device shown in FIG. 1 can be implemented as multiple, distributed systems or devices. Additionally, or alternatively, a set of systems or a set of devices (e.g., one or more systems, one or more devices) of environment 100 can perform one or more functions described as being performed by another set of systems or another set of devices of environment 100. For example, imaging system 110, control system 120, user interface 140, injector 140, and/or external data system(s) 150 may each contain computer functions that may be performed by one or more computers. The manner in which the planning of the procedure, execution of the plan, and analysis of the data acquired is partitioned between the various components or devices of the total or overall system can vary depending upon the preference of the manufacturer or manufacturers. For example, control system 120 may collect data from each of the other components and the various computers associated with injector 140 and imaging system 110, and coordinate activities of components in environment 100. As an example, control system 120 may control and coordinate injection protocols (contrast and saline) that influence the input function of the tissue of interest, imager bed position sequence and timing, collimation, mode of acquisition (2D, 3D, TGF), slice duration, data capture (list mode, in some non-limiting embodiments, for flexible reconstruction), PK/PD model used, ECG synchronization/acquisition, and the application of anatomical information from CT or MR, for example tissue boundaries to allow for significant changes in PK/PD model results.

Figure 2:
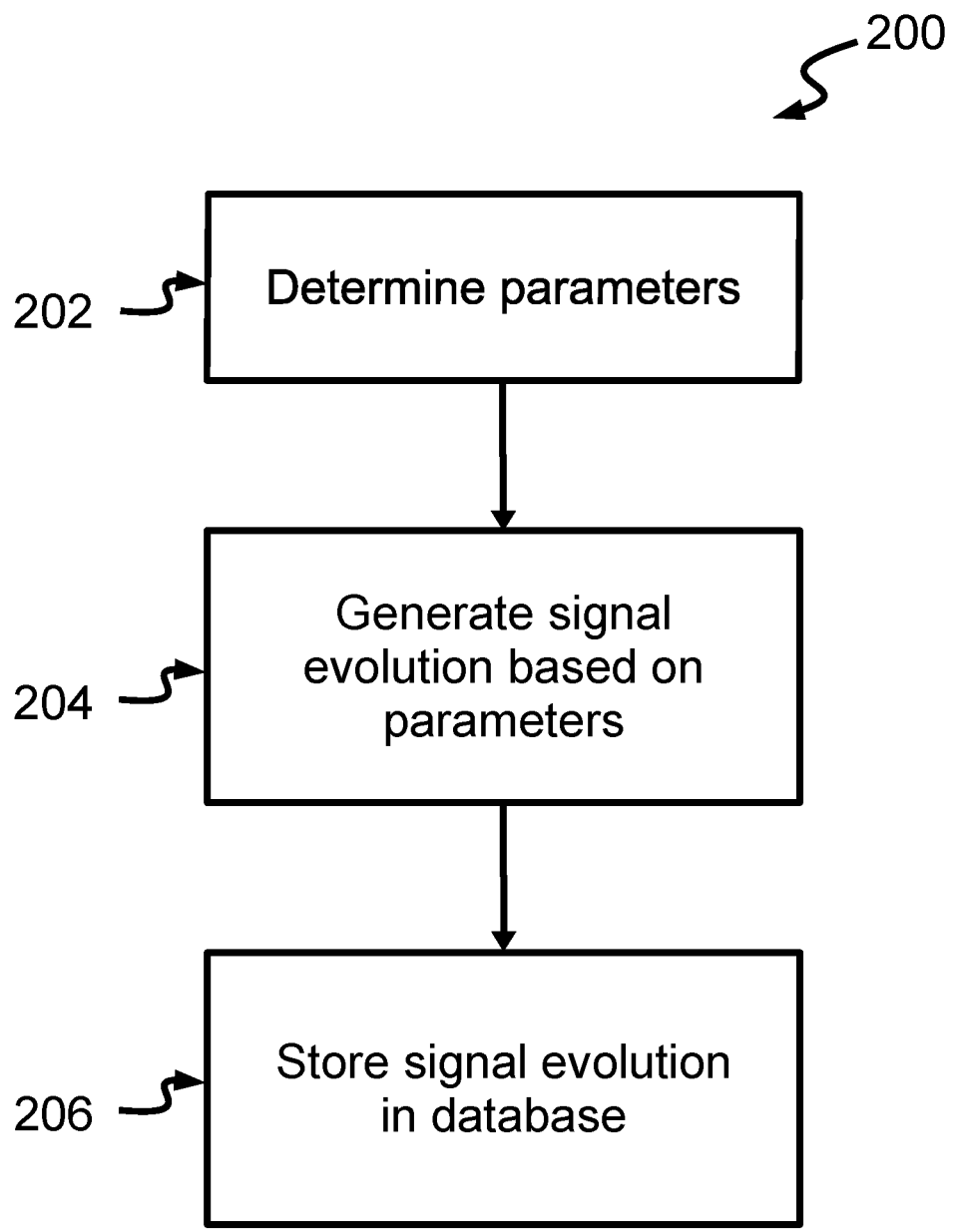
FIG. 2 is a flowchart of a non-limiting embodiment or aspect of a process described herein.

Referring now to FIG. 2, FIG. 2 is a flowchart of a non-limiting embodiment or aspect of a process 200 for generating a signal evolution that defines a contrast related parameter over time. In some non-limiting embodiments, one or more of the steps of process 200 are performed (e.g., completely, partially, etc.) by control system 120 (e.g., one or more devices of control system 120). In some non-limiting embodiments, one or more of the steps of process 200 are performed (e.g., completely, partially, etc.) by another device or a group of devices separate from and/or including control system 120, such as imaging system 110, user interface 130, injector 140, and/or external data system(s) 150 (e.g., one or more devices of imaging system 110, user interface 130, injector 140, and/or external data system(s) 150).

As shown in FIG. 2, at step 202, process 200 includes determining a plurality of parameters associated with a volume in an object over time in a series of sequence blocks. In some non-limiting embodiments, in a sequence block in the series of sequence blocks, the plurality of parameters are determined as occurring simultaneously in the volume in the object. In some non-limiting embodiments, at least one parameter of the plurality of parameters varies from the sequence block to another sequence block in the series of sequence blocks, and the plurality of parameters include a contrast related parameter associated with a concentration of a contrast agent in the volume in the object over time in the series of sequence blocks.

In some non-limiting embodiments, determining the plurality of parameters associated with the volume in the object over time in the series of sequence blocks is based on a model associated with one or more resonant species in the volume in the object. For example, the model simulates behavior of the one or more resonant species in the volume in the object in response to magnetic resonance (MR) excitation in the series of sequence blocks.

In some non-limiting embodiments, the plurality of parameters are determined as described in "Overview of Magnetic Resonance Fingerprinting by Vikas", Gulani et al., MAGNETOM Flash (65), February 2016, "Magnetic Resonance Fingerprinting," Nature, Mar. 14, 2013, Vol. 495 (7440), pp. 187-192, by Ma et al., and/or U.S. application Ser. No. 13/051,044, filed on Mar. 18, 2011, now issued U.S. Pat. No. 8,723,518, the disclosures of each of which are incorporated herein by reference in their entireties. In some non-limiting embodiments, the plurality of parameters are determined a Synthetic MR technique employing SyMRI® software developed by SyntheticMR AB for use with magnetic resonance imaging, for example, as described in U.S. application Ser. No. 13/540,027, filed on Jul. 2, 2012, no issued U.S. Pat. No. 9,618,596, and U.S. application Ser. No. 13/879,321, filed on Oct. 14, 2010, the disclosures of each of which are incorporated herein by reference in their entireties.

In some non-limiting embodiments, the contrast related parameter is determined based on data associated with the concentration of the contrast agent in blood associated with the volume over time in the series of sequence blocks. In some non-limiting embodiments, the contrast related parameter is determined based on data associated with a concentration of the contrast agent in an extracellular volume of the object over time in the series of sequence blocks and data associated with a fraction of the volume in the object including the extracellular volume over time in the series of sequence blocks. As an example, the concentration of the contrast agent in the volume over time in the series of sequence blocks is determined based on at least one of the following parameters: a concentration of the contrast agent in a blood pool of a patient over time in the series of sequence blocks, the concentration of the contrast agent in an extracellular volume of the patient over time in the series of sequence blocks, a fraction of the volume in the patient including the extracellular volume over time in the series of sequence blocks, or any combination thereof.

In some non-limiting embodiments, the concentration of the contrast agent in the blood pool of the patient over time is represented by the following equation:

$$y(t)=+B \quad (1)$$

where y(t) is the concentration of the contrast agent in the blood pool of the patient over time, t is time, and A and B are constants determined based on a model or algorithm used to estimate or simulate the contrast related parameter. For example, A and B are constants associated with parameters of the contrast fluid including the contrast agent, parameters of the patient, and/or parameters of the tissue being imaged, for example, as described in more detail herein with respect to FIG. 4 and U.S. Pat. Nos. 5,840,026, 6,385,483, and 8,295,914, assigned to the assignee of the present disclosure, the disclosures of which are incorporated by reference.

Similarly, in some non-limiting embodiments, the concentration of the contrast agent in the extracellular volume of the patient over time is represented by the following equation:

$$y'(t)=A'*t+B' \quad (2)$$

where y'(t) is the concentration of the contrast agent in the extracellular volume of the patient, t is time, and A' and B' are constants determined based on a model or algorithm used to estimate or simulate the contrast related parameter. For example, A' and B' are constants associated with parameters of the contrast fluid including the contrast agent, parameters of the patient, and/or parameters of the tissue being imaged, for example, as described in more detail herein with respect to FIG. 4 and U.S. Pat. Nos. 5,840,026, 6,385,483, and 8,295,914, assigned to the assignee of the present disclosure, the disclosures of which are incorporated by reference.

It is noted that, in a steady state dynamic equilibrium, the concentration of the contrast agent in the extracellular volume (e.g., in tissue) of the patient is following but lagging behind the concentration of the contrast agent in the blood pool of the patient. For example, in some volumes (e.g., voxels) in the patient, B may equal B', but A may not equal A'. In some non-limiting embodiments, the concentration of the contrast agent in the blood pool of the patient over time is represented by the following equation of a line with an offset in time:

$$y(t)=M*(t-\text{To}) \quad (3)$$

where M is based on the constants A and B, t is time, and To is an offset in time. This is a another way of representing the same line.

In some non-limiting embodiments, an input function for the volume in the object is determined based on data associated with the object (e.g., patient parameters, etc.), the input function providing a time enhancement output for a given input. As an example, an input function for the volume can be determined as described in more detail herein with respect to FIG. 4 and U.S. Pat. Nos. 5,840,026, 6,385,483, and 8,295,914, assigned to the assignee of the present disclosure, the disclosures of which are incorporated by reference.

In some non-limiting embodiments, a desired time enhancement output associated with the contrast related parameter is determined. For example, the desired time enhancement output can be associated with a time to achieve a desired concentration of the contrast agent over time in a blood pool of a patient and/or in the volume in the object. As an example, the desired time enhancement output can be associated with at least one of (i) a substantially constant concentration of a contrast agent in the blood pool of the patient over time, and (ii) a substantially linear rate of change in the concentration of the contrast agent in the blood pool of the patient over time, and (iii) a time varying concentration of the contrast agent utilized to generate a signal evolution for MR fingerprinting, or any combination thereof. In some non-limiting embodiments, the desired time enhancement output is associated with a minimum time to achieve the desired time enhancement output, such as a minimum time to achieve a desired concentration of the contrast parameter in the blood pool of a patient and/or in the volume over time in the series of sequence blocks. The input function for the volume can be used to determine the signal evolution defining the contrast related parameter over time in the series of sequence blocks.

As further shown in FIG. 2, at step 204, process 200 includes generating a signal evolution based on the plurality of parameters of the volume in the object over time in the series of sequence blocks, wherein the signal evolution defines the contrast related parameter over time in the series of sequence blocks. In some non-limiting embodiments, the signal evolution is generated as described in "Overview of Magnetic Resonance Fingerprinting by Vikas", Gulani et al., MAGNETOM Flash (65), February 2016, "Magnetic Resonance Fingerprinting," Nature, Mar. 14, 2013, Vol. 495 (7440), pp, 187-192, by Ma et al., and/or U.S. application Ser. No. 13/051,044, filed on Mar. 18, 2011, now issued U.S. Pat. No. 8,723,518, the disclosures of each of which are incorporated herein by reference in their entireties. In some non-limiting embodiments, the signal evolution is generated a Synthetic MR technique employing SyMRI® software developed by SyntheticMR AB for use with magnetic resonance imaging, for example, as described in U.S. application Ser. No. 13/540,027, filed on Jul. 2, 2012, no issued U.S. Pat. No. 9,618,596, and U.S. application Ser. No. 13/879,321, filed on Oct. 14, 2010, the disclosures of each of which are incorporated herein by reference in their entireties.

As an example, determining the signal evolution may include storing (k, t, E) space data points, where t is time and E includes the parameters of the volume (e.g., T1, T2, and one other relaxation parameter, T1 being spin lattice relaxation, and T2 being spin-spin relaxation, and where one or more of, t, and E, vary non-linearly) including the contrast related parameter associated with the concentration of the contrast agent in the volume over time in the series of sequence blocks.

As further shown in FIG. 2, at step 206, process 200 includes storing the signal evolution association with the volume in the object in a database. For example, the generated signal evolution is stored in a dictionary or library of signal evolutions in association with the volume in the object (e.g., in association with one or more resonant species in the volume in the object). For example, the generated signal evolution is stored as baseline signature or known signal evolution. In some non-limiting embodiments, the signal evolution defines the contrast related parameter as a linear function.

In some non-limiting embodiments, the contrast related parameter is substantially constant over time in the series of sequence blocks. In some non-limiting embodiments, the contrast related parameter changes at a substantially linear rate over time in the series of sequence blocks. In some non-limiting embodiments, the contrast related parameter is substantially constant during the sequence block. In some non-limiting embodiments, the contrast related parameter increases at a substantially linear rate over a first subset of sequence blocks in the series of sequence blocks. In some non-limiting embodiments, the contrast related parameter decreases at a substantially linear rate over a second subset of sequence blocks in the series of sequence blocks. In some non-limiting embodiments, the contrast related parameter changes exponentially over time in the series of sequence blocks.

Figure 3:
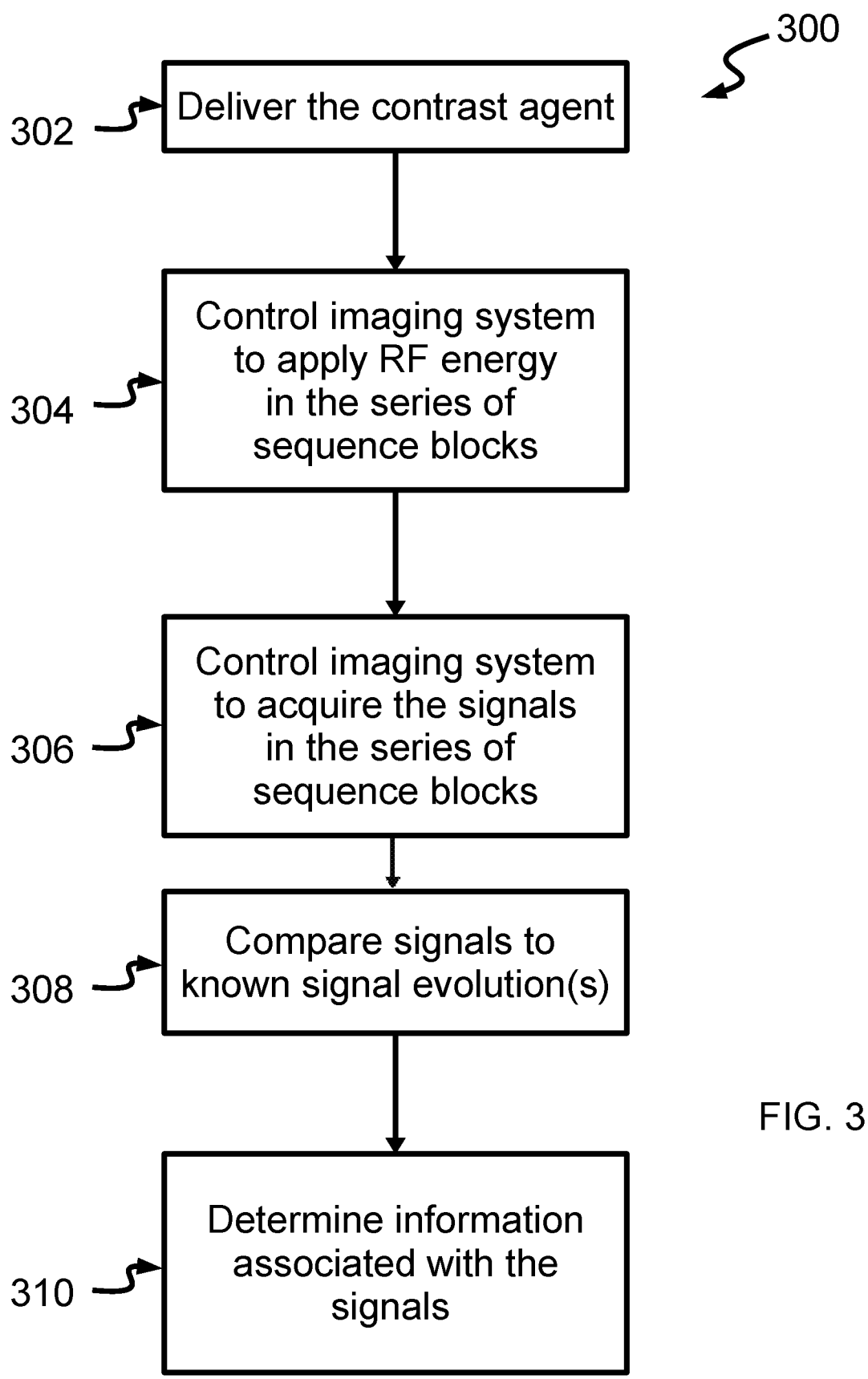
FIG. 3 is a flowchart of a non-limiting embodiment or aspect of a process described herein.

Referring now to FIG. 3, FIG. 3 is a flowchart of a non-limiting embodiment or aspect of a process 300 for measuring simultaneous produced signals from a volume in an object associated with a concentration of a contrast agent. In some non-limiting embodiments, one or more of the steps of process 300 are performed (e.g., completely, partially, etc.) by control system 120 (e.g., one or more devices of control system 120). In some non-limiting embodiments, one or more of the steps of process 300 are performed (e.g., completely, partially, etc.) by another device or a group of devices separate from or including control system 120, such as imaging system 110, user interface 130, injector 140, and/or external data system(s) 150 (e.g., one or more devices of imaging system 110, user interface 130, injector 140, and/or external data system(s) 150).

As shown in FIG. 3, at step 302, process 300 includes delivering the contrast agent. For example, the contrast agent is delivered to the blood pool of the patient including the volume in the object, (e.g., a volume in blood, tissues, bone, etc. of the patient) during a fluid delivery procedure, such as during an injection procedure. As an example, a physician or other medical personnel can deliver the contrast agent manually to the patient and/or injector 140, for example, under the control of control system 120, can deliver the contrast agent contrast to the patient.

In some non-limiting embodiments, the contrast agent is delivered to the patient in a method for delivering a medical fluid. The medical fluid can include, but is not limited to, the contrast agent, a flush fluid, and combinations thereof. The delivery of medical fluid can be part of an injection procedure in which the medical fluid including the contrast agent is delivered to a patient, though this disclosure is not limited to fluid delivery only for this purpose.

In some non-limiting embodiments, the medical fluid can be delivered according to a "protocol." As used herein with respect to a fluid delivery procedure, the term "protocol" refers to a group of parameters such as flow rate, flow volume, delivery duration, etc. that define the amount of fluid(s) to be delivered during a fluid delivery procedure, such as to a patient during an injection procedure. Such parameters can change over the course of the procedure. As used herein, the term "phase" refers generally to a group of parameters that define the amount of fluid(s) to be delivered during a period of time (or phase duration) that can be less than the total duration of the fluid delivery procedure. Thus, the parameters of a phase provide a description of the fluid delivery over a time instance corresponding to the time duration of the phase. By way of example, one parameter can be the initial total volumetric flow rate, which corresponds to the total volume of fluid per unit time being delivered at the outset of the phase. The initial total volumetric flowrate may be comprised of the fluid volume of more than one fluid, such as a first fluid and second fluid, which are being delivered simultaneously. For example, if, at the onset of a phase, a flowrate of a first fluid is 5 mL/s and a flowrate of a second fluid is 2 mL/s, the initial total volumetric flowrate would be 7 mL/s. Similarly, if the fluid delivery protocol requires only the first fluid to be delivered at the onset of the phase, again at a flow rate of 5 mL/s, while none of the second fluid is delivered at the onset of the phase, the initial total volumetric flowrate would be 5 mL/s. A fluid delivery protocol for a particular procedure can, for example, be described as uniphasic (a single phase), biphasic (two phases) or multiphasic (two or more phases, but typically more than two phases). Multiphasic procedures also include procedures in which the parameters can change continuously over at least a portion of the procedure.

In some non-limiting embodiments, phase variables or parameters as described herein are populated within a phase programming mechanism (see FIG. 1 for a non-limiting embodiment of a user interface 130 that can be used with injector 140) based on one or more parameters of interest, including, for example, but not limited to, contrast agent concentration (e.g., iodine concentration in the case of a CT procedure), a patient parameter (e.g., body weight, height, gender, age, cardiac output, etc.), the type of scan being performed, and the type of catheter inserted into the patient for intravascular access. As discussed above, differences in dosing requirements for different patients during imaging and other procedures have been recognized. For example, U.S. Pat. Nos. 5,840,026 and 6,385,483, assigned to the assignee of the present disclosure, the disclosures of which are incorporated herein by reference, disclose devices and methods to customize the injection to the patient using patient specific data derived before or during an injection. Likewise, U.S. Pat. No. 8,295,914, assigned to the assignee of the present disclosure, the disclosure of which is incorporated herein by reference, also discloses customization of injections to a patient using patient specific data and sets forth a number of models to describe a time enhancement output for a given input or protocol.

A clinical operator can control injector 140 by entering volumes and/or flow rates into fields provided on user interface 130 by selecting a pre-defined protocol, and/or by using control system 120 to compute a protocol. Control system 120 can compute an injection protocol for the delivery of a fluid volume over time where the fluid volume includes at least a volumetric amount of a first fluid, such as contrast agent, delivered at a flowrate that may vary over time and may be zero at certain times, and a volumetric amount of a second fluid, such as saline, which also may be delivered at a flowrate that may vary over time and may be zero at certain times. In some non-limiting embodiments, a threshold for a constant volumetric flow to be delivered by injector 140 is greater than 0.5 ml/s if the fluid is being delivered to an arm of a patient.

The injection protocol can be determined by first determining the parameters (e.g., total volume, flowrate over time, etc.) for delivering the contrast agent. For purposes of this disclosure, the parameters for delivering a contrast agent may be collectively referred to as the "contrast agent protocol." The software can follow, for example, any of a variety of known models for determining the contrast agent protocol. These include, but are not limited to, contrast agent protocols that have been developed to achieve a desired bolus profile or shape.

In some non-limiting embodiments, the delivery of contrast agent can follow contrast agent protocols described in U.S. Pat. Nos. 6,055,985, 6,635,030, 6,470,889 each to Bae et al., the entire contents of each of which are incorporated herein by reference. Bae et al. describe a methodology for determining a protocol for delivering a contrast agent to a patient which attempts to optimize the use of contrast agent to achieve an enhancement in excess of a preselected threshold and to maintain that excess level of enhancement for a temporal duration that is near optimal given the amount of contrast used.

For example, in U.S. Pat. No. 6,055,985, Bae et al. set forth various ramped, or multiphasic, or exponentially decaying, or steadily decreasing injection rates. Bae et al, solve a set of differential equations describing a simplified compartment model of a patient's body to render an exponentially decaying rate of contrast injection having a particular decay coefficient, though it was contemplated that in the real world, this exponentially decaying injection rate could be approximated by a linear decay, or ramped decay, or even a multi-step decay. The particular decay coefficient calculated by Bae et al. is proportional to the cardiac output per body weight of the patient and is approximated to be 0.01.

In some non-limiting embodiments of Bae et al., the contrast agent protocol is determined by an initial delivery rate and an exponential decay coefficient. This is illustrated in FIG. 3 of U.S. Pat. No. 6,055,985. The initial delivery rate can be, for example, 2 mL/s. The total injected volume of contrast agent corresponds to the integrated sum of the injection over the injection duration. The total injected volume of contrast agent can be, for example, 50 mL, 70 mL, or 90 mL. Bae et al. also disclose an exponential decay coefficient equal to Q/Vs, which is the ratio of cardiac output (Q) to the systematic volume of distinction of contrast medium, which itself is proportional to the cardiac output per body weight (Vs). Bae et al. disclose and focus on decay coefficients at or near 0.01, 0.02, and 0.03 and an injection duration of 120 seconds.

Bae et al. propose a contrast injection routine where an interval of the routine begins at a preselected initial flowrate of contrast agent and then the flowrate is controllably decreased during the routine at substantially an exponential rate having a decay coefficient that approximates the cardiac output per body weight that is typical of the patient. Bae et al. also teach that functional patterns other than an exponential decay may be used to deliver the contrast agent, including approximating a short segment of an exponential curve by a linear or ramped contrast injection protocol. Bae et al, provide an exemplary contrast injection protocol in which delivery of a contrast agent begins at a preselected initial injection flowrate and then the flowrate is controllably decreased, such as along a path of exponential decay, until the desired volume of contrast has been delivered and/or the desired injection duration has elapsed. For example, in U.S. Pat. No. 6,470,889, Bae et al. describes a truncated exponential delay to achieve relatively uniform high contrast agent levels for a relatively short period of time (e.g., about 30 seconds), and the contrast agent concentration levels in the blood decay after the injection is stopped. However, this truncated exponential delay described in Bae et al. results in an undesirable overshoot in the concentration of the contrast agent level.

Techniques described by Bae et al. can be applied to the present disclosure as a method of delivering a volumetric amount of a contrast agent by controllably varying the flowrate of the contrast agent during at least a portion of the injection procedure. For example, a contrast agent protocol for a particular patient can be determined according to the process set forth by Bae et al. This contrast agent protocol can form part of the injection protocol, and particularly the portion of the injection protocol that controls the delivery of a contrast agent.

In some non-limiting embodiments, delivery of a contrast agent can follow a contrast agent protocol described in the article "Mathematical Analysis of Arterial Enhancement and Optimization of Bolus Geometry for CT Angiography Using the Discrete Fourier Transform," Journal of Computer Assisted Tomography, Volume 23(3), May/June 1999, pp. 474-484, by Fleischmann et al., the entire contents of which are incorporated by reference.

Fleischmann et al. describe a mathematical technique for the analysis of an individual patient's contribution, referred to therein as the "patient function," to the patient's time-attenuation response to intravenously injected contrast material. Fleischmann et al. assert that their technique can be used to predict the time-attenuation response to a given contrast agent bolus injection and calculate individually "optimized" injection parameters, which aims to achieve a uniform arterial opacification at a pre-defined level of enhancement for the entire scanning.

According to Fleischmann et al., a small bolus injection, a test bolus injection, of contrast agent (16 ml of contrast at 4 ml/s) is made prior to a diagnostic scan. A dynamic enhancement scan is then made across a vessel of interest. The resulting processed scan data (test scan) is interpreted as the impulse response of the patient/contrast medium system. Fleischmann et al. derived the Fourier transform of the patient transfer function by dividing the Fourier transform of the test scan by the Fourier transform of the test injection. Assuming the system was a linear time invariant (LTI) system and that the desired output time domain signal was known (a flat diagnostic scan at a predefined enhancement level); Fleischmann et al. derived an input time signal by dividing the frequency domain representations of the desired output by that of the patient transfer function. Because the method of Fleischmann et al. computes input signals that are not realizable in reality as a result of injection system limitations (for example, flow rate limitations), one must truncate and approximate the computed continuous time signal.

Fleischmann et al. further describe a technique to characterize, predict, and optimize enhancement using a set of mathematical relations. The relations can be assembled into a notebook file of a commercially available computer program (Mathematica for Windows, enhanced version 2.2.3; Wolfram Research, Champaign, Ill., U.S.A.). The Mathematica notebook requires the input of (a) the test bolus, (b) the corresponding test enhancement, (c) the parameters of an arbitrary standard bolus, and finally (d) the desired "ideal" arterial enhancement.

To predict enhancement and to calculate an optimized injection bolus for an individual, the following steps were implemented by Fleischmann et al. Step 1: from the parameters (volume, flow rate) of the test bolus and the corresponding arterial time-attenuation response, the program calculates the patient function in the Fourier space from the relation of a test bolus to a patient's corresponding aortic time-attenuation response; the test enhancement. The patient function plays the central role in predicting the individual enhancement response to a given bolus (e.g., a standard uniphasic injection), as well as in calculating the "ideal" injection parameters for a theoretically ideal (near rectangular) enhancement curve. Step 2: once the patient function is known, the standard enhancement to an arbitrary bolus, e.g., a 120 ml standard bolus, can be predicted. Step 3: with the use of the patient function, calculate a theoretically "ideal" bolus, which should achieve a near rectangular enhancement. Step 4: since the theoretically "ideal bolus" contains "unreal" components in the time domain, like oscillations, or negative flow rates, a fitting algorithm is introduced to approximate the ideal flow rates into a practically applicable optimized biphasic bolus. The corresponding optimized enhancement can be predicted as described in Step 2, Step 4 represents an independently developed fitting process in the time domain.

Techniques described by Fleischmann et al. can be applied to the present disclosure as a method of delivering a volumetric amount of a contrast agent by controllably varying the flowrate of the contrast agent during a least a portion of the injection procedure. For example, a contrast agent protocol for a particular patient can be determined according to the process set forth by Fleischmann et al. This contrast agent protocol can form part of the injection protocol, and particularly the portion of the injection protocol that controls the delivery of a contrast agent.

In some non-limiting embodiments, delivery of a contrast agent can follow a contrast agent protocol described in the article "A general method for calculating the dosage scheme in linear pharmacokinetics," European Journal of Clinical Pharmacology, Volume 20(5), 1981, pp. 379-386, by H. Schwilden, the entire contents of which are incorporated by reference. H. Schwilden describes delivery of a drug with an exponential decay to a constant infusion rate that achieves a constant blood pool level of a drug being injected over relatively long timeframes (e.g., many tens of minutes).

In some non-limiting embodiments, delivery of a contrast agent can follow a protocol described in related International Application No. PCT/US2017/62728, assigned to the assignee of the present disclosure and filed concurrently herewith on Nov. 21, 2017, which claims the benefit of U.S. Provisional Application No. 62/425,312, filed Nov. 22, 2016, the entire disclosure of which is incorporated by reference. Concurrently filed International Application No. PCT/US2017/62728 describes delivering a fluid volume at a substantially consistent total volumetric flowrate, the provision of which over the whole delivery of the contrast and flushing fluid enables the bolus shape in the tissue of interest to be closer to what is expected or predicted and less dependent on patient to patient variation as well as variations for the same patient over time, which enables better scan timing and more consistent image quality and, by reducing variation, reduces radiation and/or contrast media volumes as well.

The above described injection protocols and contrast agent protocols are intended to be exemplary only. One of skill in the art would recognize, upon reading the present disclosure, that non-limiting embodiments or aspects may employ other injection protocols and contrast agent protocols, including other protocols in which the flowrate of contrast varies over time.

In some non-limiting embodiments, it is preferable to start an imaging procedure after a contrast agent is uniformly distributed in a blood pool of a patient (e.g., a concentration of the contrast agent in the blood pool is substantially steady). For example, a relatively controlled blood pool level or concentration of a contrast agent simplifies incorporation of a contrast related parameter associated with the concentration of the contrast agent into a process used to model MR signals and create images from the MR signals. Furthermore, as discussed herein, in some non-limiting embodiments, it is preferable to achieve a uniform blood pool concentration level of a contrast agent as quickly as possible as compared to the normal practice which has been to inject a blood pool agent and waiting sufficient time, for example 1.5 to 2 minutes.

In some non-limiting embodiments, the concentration of the contrast agent in the blood is substantially constant over time in the series of sequence blocks. For example, delivering the contrast agent includes controlling an injector to deliver the contrast agent based on an injection protocol associated with achieving the substantially constant concentration of the contrast agent in the blood pool of the patient over time in the series of sequence blocks (e.g., an injection protocol including a contrast agent protocol in which a delivery rate of a blood pool contrast agent decays exponentially over time from an initial delivery rate). As an example, control system 120 controls injector 140 to deliver the blood pool contrast agent (e.g., ferumoxytol, etc.) via a bolus injection according to a decayed exponential injection protocol (e.g., of either exponentially decaying concentration or flow rate), optionally with a constant total volumetric flow rate, to facilitate achieving a steady state blood concentration of the blood pool contrast agent as quickly as possible. After the steady state blood concentration of the blood pool contrast agent is achieved, which can be determined based on an estimation, simulation, and/or measurement of blood pool contrast agent concentration level, control system 120 controls imaging system 110 to start an imaging procedure (e.g., an MR fingerprinting imaging process) as described in more detail herein with respect to steps 304 and 306 of process 300 in FIG. 3. Because a blood pool contrast agent does not typically diffuse into tissue, the concentration of the blood pool contrast agent in the blood is relatively stable over time in the series of sequence blocks. Control system 120 can generate the information associated with the concentration of the contrast agent in the volume based on a concentration of the blood pool contrast agent in the blood pool that is substantially constant over time in the series of sequence blocks and, in some non-limiting embodiments, a fraction of the volume filled with blood at the constant blood pool concentration of the contrast agent. For example, in some non-limiting embodiments, it is desirable to use each of these variables in a model because the response of various MR parameters is a non-linear function of the concentration of the contrast agent in the volume or voxel (unlike CT parameters which have a generally linear relationship between Hounsfield units and iodine density).

In some non-limiting embodiments, the concentration of the contrast agent in the blood changes at a substantially linear rate over time in the series of sequence blocks. For example, delivering the contrast agent includes controlling injector 140 to deliver the contrast agent based on an injection protocol associated with achieving the concentration of the contrast agent in the blood pool of the patient that changes at the substantially linear rate over time in the series of sequence blocks.

In some non-limiting embodiments, the concentration of the contrast agent in the blood increases at a substantially linear rate over the series of sequence blocks. For example, in some non-limiting embodiments, it is preferable to have a consistently increasing level of contrast agent (e.g., a linearly increasing concentration level of a diffusible contrast agent) in the blood pool of the patient during imaging (e.g., over the series of sequence blocks). As an example, delivering the contrast agent includes controlling an injector to deliver the contrast agent during a delivery procedure based on at least one of the following injection protocols: a first injection protocol in which a delivery rate of the contrast agent is constant over an entire time of the delivery procedure; a second injection protocol in which, in a first interval of the delivery procedure, the delivery rate of the contrast agent is an initial constant delivery rate, and, in a second interval of the delivery procedure after the first interval, the delivery rate of the contrast agent is a subsequent constant delivery rate less than the initial constant delivery rate, wherein the second interval is longer than the first interval; and a third injection protocol in which, the delivery rate of the contrast agent decays exponentially over time from an initial delivery rate to a subsequent lower delivery rate at which the delivery rate of the contrast agent is held constant through a remainder of the delivery procedure.

Figure 4A:
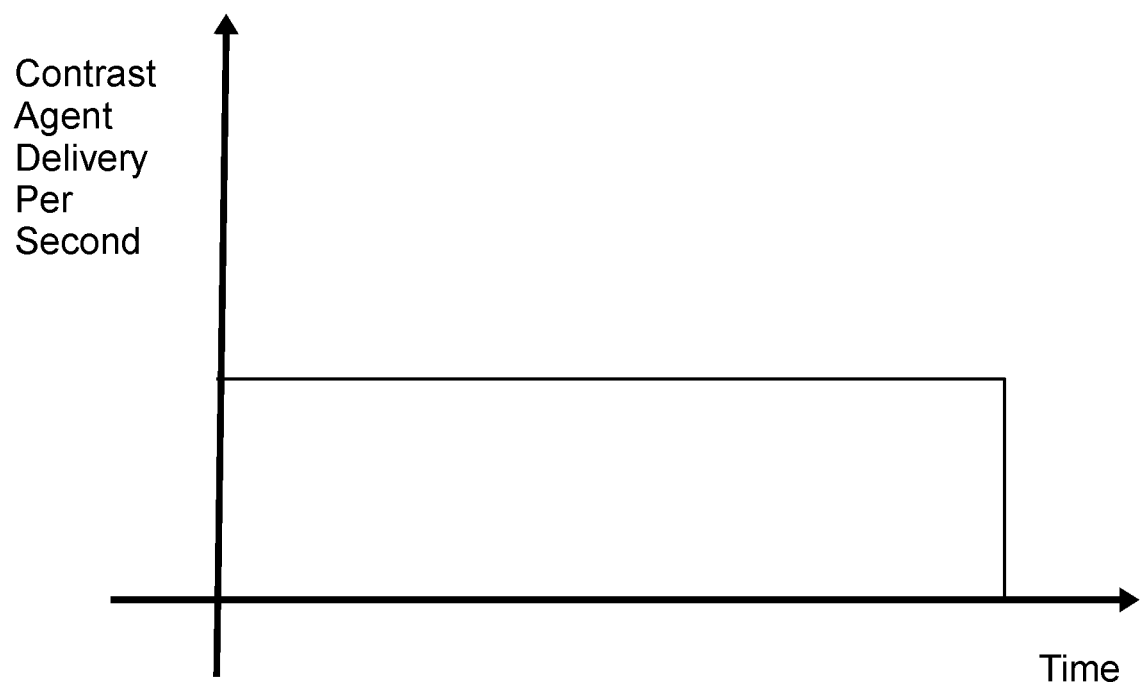
FIGS. 4A-4C are graphs of example injection protocols for achieving a concentration of a contrast agent in a blood pool of a patient that increases at a substantially linear rate over time in implementations of a non-limiting embodiment or aspect of a process described herein.
Figure 4B:
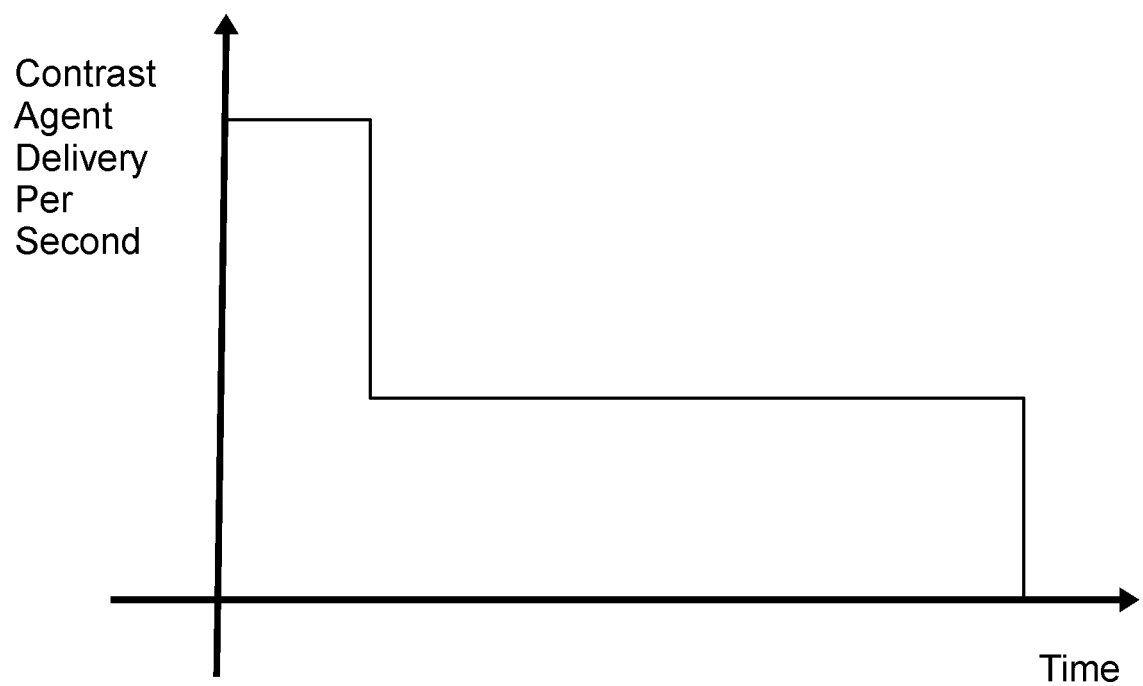
Figure 4C:
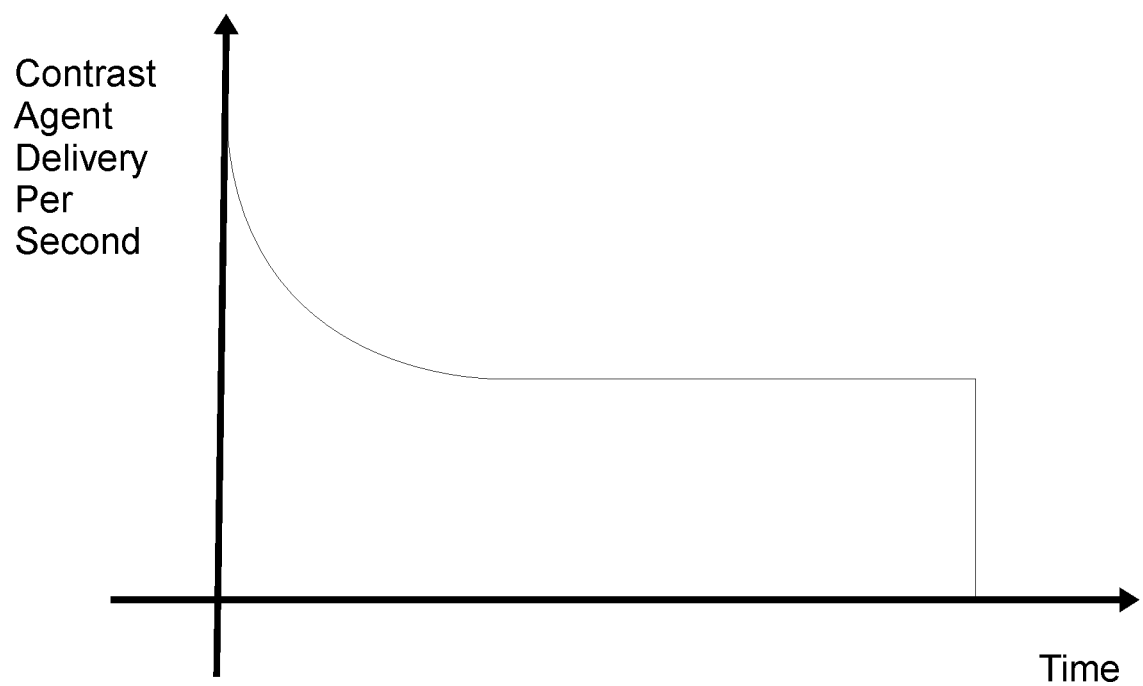
Figure 4D:
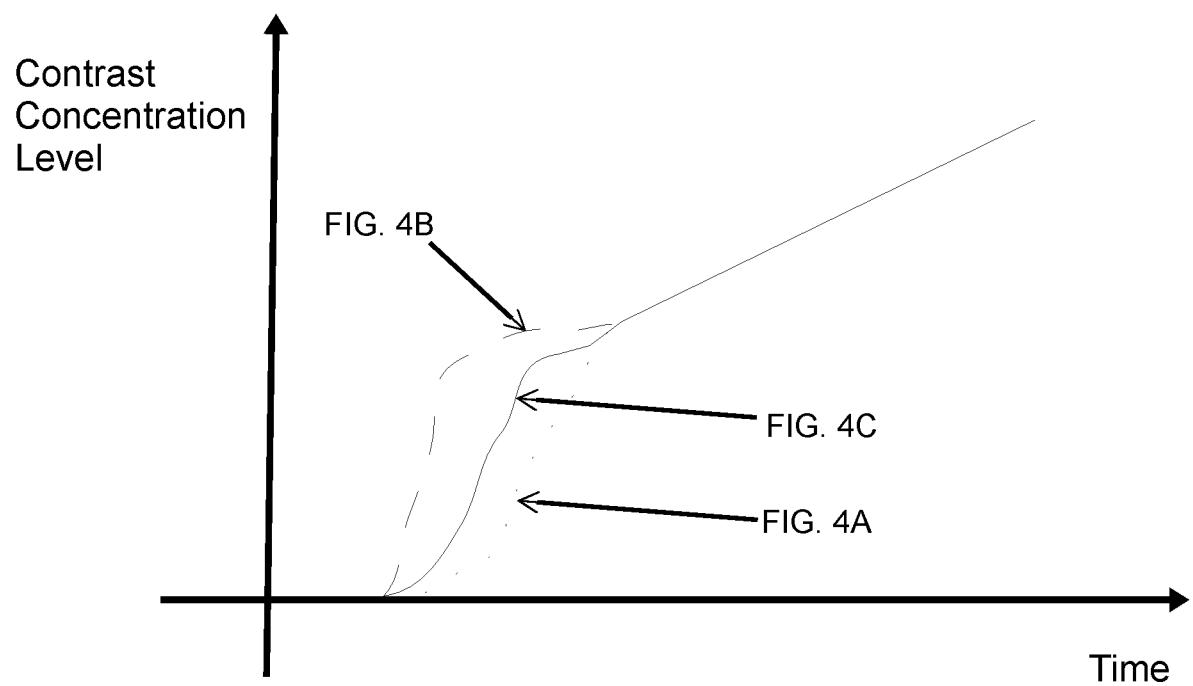
FIG. 4D is a graph of example concentrations of the contrast agent in a blood pool of a patient over time in the implementations of FIGS. 4A-4C.

FIGS. 4A-4C are graphs of example implementations of injection protocols for achieving a concentration of a contrast agent in a blood pool of a patient that increases at a substantially linear rate over time. FIG. 4D is a graph of example implementations of concentrations of the contrast agent in a blood pool of a patient over time in FIGS. 4A-4C. As an example, in the first injection protocol, the substantially linear increase in the concentration of the contrast agent in the blood over time in the series of sequence blocks can be provided based on an injection protocol as shown in FIG. 4A, in which a delivery rate of the contrast agent is constant over an entire time of the delivery procedure. For example, control system 120 controls injector 140 to deliver a diffusible contrast agent at a substantially steady contrast agent delivery level from the start of the delivery procedure and controls the imaging system 110 to delay the imaging procedure from the start of the delivery procedure (e.g., about 20-120 seconds from the start of the delivery procedure) to allow an initial equilibration of the diffusible contrast agent throughout the blood pool in the body of the patient.

As an example, in the second injection protocol, the substantially linear increase in the concentration of the contrast agent in the blood over time in the series of sequence blocks can be provided based on an injection protocol as shown in FIG. 4B, in which in the first interval of the delivery procedure, the delivery rate of the contrast agent is an initial constant delivery rate, and, in the second interval of the delivery procedure after the first interval, the delivery rate of the contrast agent is a subsequent constant delivery rate less than the initial constant delivery rate, with the second interval being longer than the first interval. For example, control system 120 controls injector 140 to deliver a diffusible contrast agent in a two phase injection with an initial higher constant contrast agent delivery rate followed by a longer and lower steady state contrast delivery rate, which can reduce a time to achieve the substantially linear increase in the concentration of the diffusible contrast agent in the blood over time, and controls imaging system 110 to delay the imaging procedure from the start of the delivery procedure to allow an initial equilibration of the diffusible contrast agent throughout the blood pool in the body of the patient.

As an example, in the third injection protocol, the substantially linear increase in the concentration of the contrast agent in the blood over time in the series of sequence blocks can be provided based on an injection protocol as shown in FIG. 4C, in which in which, the delivery rate of the contrast agent decays exponentially over time from an initial delivery rate to a subsequent lower delivery rate at which the delivery rate of the contrast agent is held constant through a remainder of the delivery procedure. For example, control system 120 controls injector 140 to deliver a diffusible contrast agent at an initial contrast agent delivery rate that decays exponentially over time until the contrast agent delivery rate satisfies a threshold rate, and maintain the contrast agent delivery rate at the threshold rate over the remainder of the delivery procedure.

It is noted that specific flow rates and durations for various injection phases discussed with respect to FIGS. 4A-4C may be dependent on parameters of the contrast fluid including the contrast agent, parameters of the patient, and/or parameters of the tissue being imaged, for example, as described in more detail herein with respect to FIG. 4 and U.S. Pat. Nos. 5,840,026, 6,385,483, and 8,295,914, assigned to the assignee of the present disclosure, the disclosures of which are incorporated by reference.

In some non-limiting embodiments, delivering the contrast agent comprises controlling an injector to deliver the contrast agent during the delivery procedure based on the contrast related parameter to provide the concentration of the contrast agent in the blood over time in the series of sequence blocks. For example, delivering the contrast agent includes controlling an injector to deliver the contrast agent based on an injection protocol associated with achieving a concentration of the contrast agent in the blood pool of the patient over time in the series of sequence blocks associated with and/or defined by the contrast related parameter associated with the series of sequence blocks.

In some non-limiting embodiments, the concentration of the contrast agent in the blood is substantially constant during or over a sequence block. For example, a rate of increase in the concentration of the contrast agent in the blood over time can be a rate of increase that provides a substantially constant concentration of the contrast during or over an individual sequence block in the series of sequence blocks (e.g., during or over MR excitation of the volume and simultaneous acquisition of the individual signals in an individual sequence block in the series of sequence blocks). In some non-limiting embodiments, the concentration of the contrast agent in the blood is substantially constant over acquisition of an image or data piece of an imaging process, for example, over acquisition of an X-ray fluoroscopy frame, a CT-spin 180°+angle (e.g., a single angle projection), one or more PET coincidence events, and/or the like. Such a substantially constant concentration of the contrast agent during or over an individual sequence block (or image/signal acquisition) reduces motion blur in captured images due to movement or other dynamic phenomena, improves accuracy in capturing and characterizing dynamic phenomena in captured images, and/or enables using measurements for modeling patient assessment and diagnosis.

In some non-limiting embodiments, the concentration of the contrast agent in the blood increases at a substantially linear rate over a first subset of sequence blocks in the series of sequence blocks, and the concentration of the contrast agent in the blood decreases at a substantially linear rate over a second subset of sequence blocks in the series of sequence blocks. For example, delivering the contrast agent includes controlling an injector to deliver the contrast agent based on an injection protocol associated with achieving a concentration of the contrast agent in the blood pool of the patient that increases at a substantially linear rate over time in the first subset of sequence blocks in the series of sequence blocks and decreases at a substantially linear rate over time in the second subset of sequence blocks in the series of sequence blocks.

In some non-limiting embodiments, the concentration of the contrast agent in the blood increases at a substantially linear rate over time in the series of sequence blocks from which the plurality of signals are acquired and information associated with the concentration of the contrast agent in the volume over time in the series of sequence blocks is generated, and the concentration of the contrast agent in the blood decreases at a substantially linear rate over time in another series of sequence blocks from which a plurality of other signals from the volume exposed to MR excitation in another series of sequence blocks are acquired and other information associated with the concentration of the contrast agent in the volume in the other series of sequence blocks generated. For example, control system 120 can apply a first MR fingerprinting imaging process to generate a first signal evolution for a volume during a first time period in which the concentration of the contrast agent in the blood increases at a substantially linear rate over time and apply a second MR fingerprinting imaging process to generate a second signal evolution for the volume during a second time period in which the concentration of the contrast agent in the blood decreases at a substantially linear rate over time.

As further shown in FIG. 3, at step 304, process 300 includes controlling an imaging system to apply radio frequency (RF) energy to the volume in the object in the series of sequence blocks to expose the volume to the MR excitation in the series of variable sequence blocks. For example, control system 120 controls imaging system 110 (e.g., a nuclear magnetic resonance (NMR) imager) to apply RF energy to a volume in an object. The volume may contain one or more resonant species. In some non-limiting embodiments, the object is a patient and the resonant species may include, but are not limited to, tissue, fat, water, hydrogen, and prosthetics.

In some non-limiting embodiments, the RF energy is applied in a series of variable sequence blocks. In some non-limiting embodiments, sequence blocks vary in a number of parameters including at least one of the following parameters: echo time, flip angle, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, type of gradient applied between a readout portion of a sequence block and an excitation portion of a sequence block, number of gradients applied between a readout portion of a sequence block and an excitation portion of a sequence block, type of gradient applied during a readout portion of a sequence block, number of gradients applied during a readout portion of a sequence block, amount of RF spoiling, amount of gradient spoiling, and/or the like. In some non-limiting embodiments two, three, four, or more parameters vary between sequence blocks. In some non-limiting embodiments, the number of parameters varied between sequence blocks may itself vary. For example, A1 (sequence block 1) may differ from A2 in five parameters, A2 may differ from A3 in seven parameters, and A3 may differ from A4 in two parameters. One skilled in the art will appreciate that there are a nearly infinite number of series of sequence blocks that can be created by varying this large number of parameters. In one embodiment, a series of sequence blocks is crafted so that the series have different amounts (e.g., 1%, 2%, 5%, 10%, 50%, 99%, 100%) of unique sequence blocks as defined by their varied parameters. In different embodiments, a series of sequence blocks may include more than ten, more than one hundred, more than one thousand, more than ten thousand, and more than one hundred thousand sequence blocks.

In some non-limiting embodiments, sequence blocks vary in a number of parameters including at least one of the following parameters: the amount of time between sequence blocks, the relative amplitude of sequence blocks, the relative phase of sequence blocks, and/or the like. For example, not only can the individual parameters (e.g., flip angle, phase, etc.) be varied between sequence blocks, but the times between sequence blocks and other differences between sequence blocks can be varied. This facilitates creating additional signal content in a signal evolution. As an example, in some non-limiting embodiments, sequence blocks vary based on the contrast related parameter, for example, in a concentration of a contrast agent in the blood pool (and/or volume being imaged) of the patient between sequence blocks. For example, the concentration of the contrast agent in the blood pool of the patient can vary in a substantially linear manner between sequence blocks in the series of sequence blocks. In some non-limiting embodiments, other parameters of sequence blocks vary based on the contrast related parameter. For example, a parameter of a sequence block can change based on an expected change in the concentration of the contrast agent in the blood pool (and/or volume being imaged) of the patient associated with and/or defined by the contrast related parameter of the sequence block. In some non-limiting embodiments, a conventional MRI scan can be interleaved with the series of sequence blocks to track a location of a bolus, for example, to track a location of a bolus during a synthetic MR imaging process.

In some non-limiting embodiments, a calibration phantom is placed in imaging system 110 with a patient to calibrate imaging system 110 as described and illustrated in GE Lunar Corp brochure SL172E 7/01 copyright 2001, the entire disclosure of which is incorporated herein by reference, which allows translation of reconstructed Hounsfield units to absolute Hounsfield units. In some non-limiting embodiments, fat, bone, and/or muscle tissue of the patient, rather than external regions of interest, are used in calibration of imaging system 110; however, such a fat, bone, and/or tissue based calibration may only work in some instances, because the tissues are of constant Hounsfield units only until the contrast agent begins to reach that tissue. For example, such a fat, bone, and/or tissue based calibration is more likely to work where the imaging target or region of interest is the lungs, heart, or great vessels and tissues, such as the spine and esophagus. Use of the tissue of the patient for calibration may also be more applicable to a test injection or the beginning of an imaging injection than to the mid or later parts of an imaging injection. In MR imaging, a phantom may include tubes or other vessels filled with the contrast agent being used in the imaging study in a wide range of concentrations, preferably covering those expected in the body. These tubes can be used as a quality check that the overall imaging procedure is performing as expected.

In some non-limiting embodiments, the RF energy applied during a sequence block is configured to cause different individual resonant species to simultaneously produce individual signals (e.g., simultaneously produce individual NMR signals). Unlike conventional MR imaging systems; at least one member of the series of variable sequence blocks differs from at least one other member of the series of variable sequence blocks in at least N sequence block parameters, N being an integer greater than one (e.g., an integer greater than two, etc.), with the signal content of a signal evolution varying directly with N such that as more parameters are varied, a potentially richer signal is retrieved.

Figure 5:
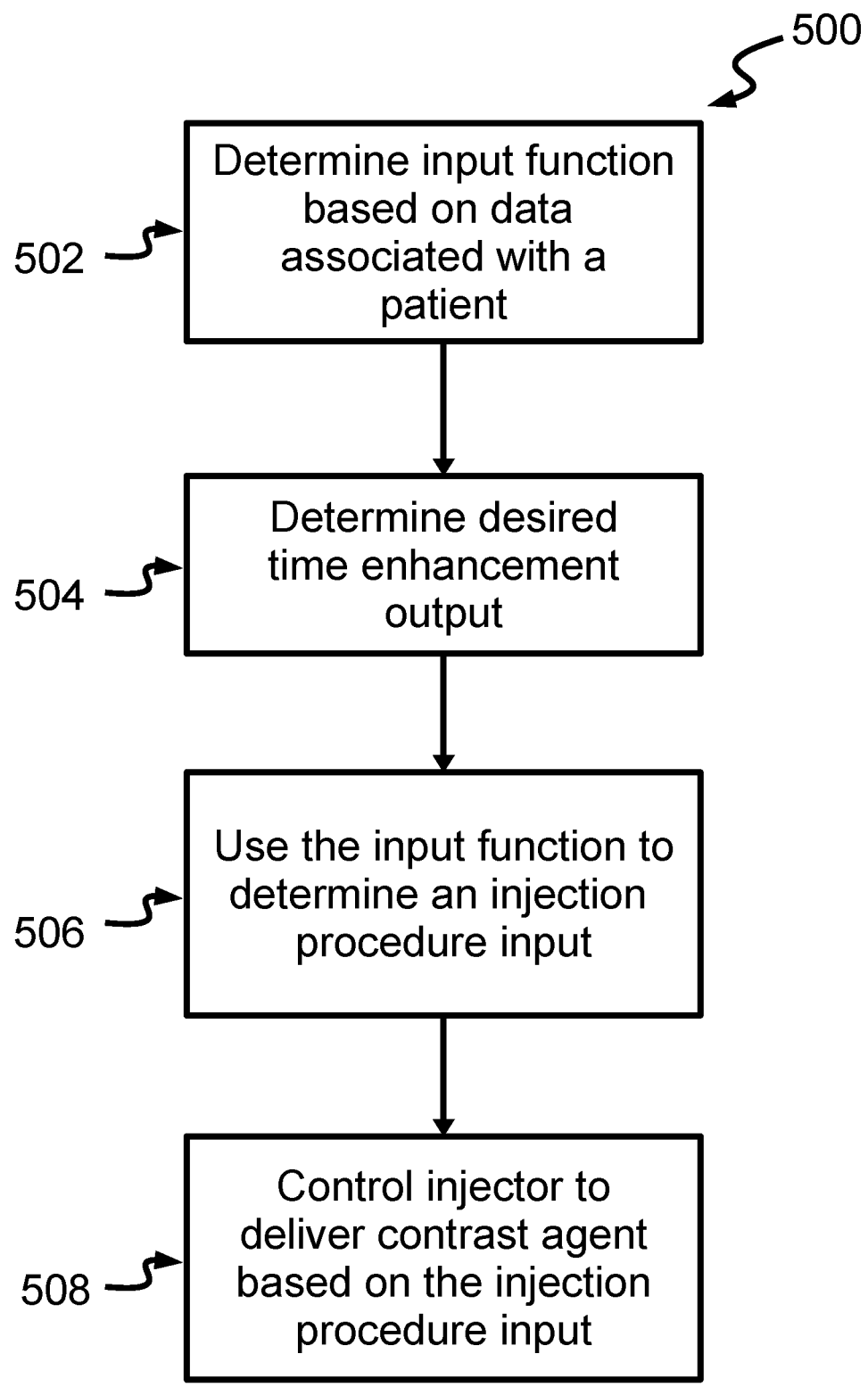
FIG. 5 is a flowchart of a non-limiting embodiment or aspect of a process described herein.

In some non-limiting embodiments, imaging system 110 is controlled to image the patient based on a determined injection protocol input as described in more detail herein with respect to FIG. 5. For example, control system 120 can control imaging system 110 to delay imaging until a desired concentration of the contrast agent (e.g., a uniform blood contrast agent level, a constant contrast agent level, a linearly changing contrast agent level, etc.) is present in the blood pool of the patient. As an example, control system 120 can determine the desired concentration of the contrast agent based on an estimation, simulation, and/or measurement of the contrast agent concentration level as described herein.

As further shown in FIG. 3, at step 306, process 300 includes controlling an imaging system to acquire the plurality of signals in the series of sequence blocks. For example, control system 120 controls imaging system 110 (e.g., a nuclear magnetic resonance (NMR) imager) to acquire the plurality of signals in the series of sequence blocks. In some non-limiting embodiments, control system 120 controls imaging system 110 to acquire the plurality of signals (e.g., scan the volume) before delivery of the contrast agent, during delivery of the contrast agent, after delivery of the contrast agent, when a concentration of the contrast agent is stabilized in a blood pool of a patient, when the concentration of the contrast agent is linearly rising and/or linearly falling in the blood pool of the patient, and/or any combination thereof. For example, control system 120 controls imaging system 110 including an NMR apparatus to acquire simultaneously produced individual NMR signals in each sequence block in the series of sequence blocks. Unlike conventional MR systems where the time during which an imaging-relevant NMR signal can be acquired is severely limited (e.g., 4-5 seconds), the NMR apparatus can be controlled to acquire NMR signal for significantly longer periods of time. For example, the NMR apparatus can be controlled to acquire signals for up to ten seconds, for up to twenty seconds, for up to one hundred seconds, or longer. NMR signals can be acquired for longer periods of time because signal information content remains viable for longer periods of time in response to the series of varied RF energy applied in the series of varied sequence blocks.

In some non-limiting embodiments, a sequence block in the series of sequence blocks is associated with a plurality of parameters, and the plurality of parameters is associated with the MR excitation in the sequence block. For example, the MR excitation in the sequence block causes one or more resonant species in the volume to simultaneously produce individual signals, and the plurality of signals comprise the simultaneously produced individual signals. As an example, the sequence block differs from another sequence block in the series of sequence blocks in two or more parameters of the plurality of parameters, and the plurality of parameters include a contrast related parameter associated with a concentration of a contrast agent in blood associated with the volume (e.g., in a blood pool of a patient including the volume).

In some non-limiting embodiments, the plurality of signals are received from a volume (e.g., a voxel) in an object (e.g., a patient) exposed to magnetic resonance (MR) excitation in a series of sequence blocks in a synthetic MR imaging procedure and/or a MR fingerprinting imaging procedure. For example, the plurality of signals are generated, acquired, and/or received from the volume in the object in a MR fingerprinting technique as described in the article "Magnetic Resonance Fingerprinting," Nature, Mar. 14, 2013, Vol. 495(7440), pp. 187-192, by Ma et al., and/or U.S. application Ser. No. 13/051,044, filed on Mar. 18, 2011, now issued U.S. Pat. No. 8,723,518, the disclosures of each of which are incorporated herein by reference in their entireties. As an example, the plurality of signals are generated, acquired, and/or received from the volume in the object in a Synthetic MR technique employing SyMRI® software developed by SyntheticMR AB for use with magnetic resonance imaging, for example, as described in U.S. application Ser. No. 13/540,027, filed on Jul. 2, 2012, no issued U.S. Pat. No. 9,618,596, and U.S. application Ser. No. 13/879,321, filed on Oct. 14, 2010, the disclosures of each of which are incorporated herein by reference in their entireties. Further details regarding step 202 of process 200 are provided below with regard to FIGS. 3 and 4.

As shown in FIG. 3, at step 308, process 300 includes comparing the plurality of signals to one or more known signal evolutions. In some non-limiting embodiments, the one or more known signal evolutions are associated with one or more known resonant species and known values of the concentration of the contrast agent in blood associated with the one or more known resonant species. For example, control system 120 compares the plurality of signals to one or more known, stored, simulated, and/or predicted signal evolutions (e.g., in the library or database of known signal evolutions) using a pattern matching process as described in in the article "Magnetic Resonance Fingerprinting," Nature, Mar. 14, 2013, Vol. 495(7440), pp. 187-192, by Ma et al., and/or U.S. application Ser. No. 13/051,044, filed on Mar. 18, 2011, now issued U.S. Pat. No. 8,723,518, the disclosures of each of which are incorporated herein by reference in their entireties. In some non-limiting embodiments, the "stored" signal evolutions may include previously acquired signals, for example, signal evolutions generated as described with respect to FIG. 3 herein, simulated signals, or both. In some non-limiting embodiments, the stored signal evolutions are associated with signals not acquired from the object or patient, and in some non-limiting embodiments the stored signal evolutions are associated with signals acquired from the object or patient.

As further shown in FIG. 3, at step 310, process 300 includes determining information associated with the signals. For example, control system 120 matches the received signals to known signals for which a reconstruction, relaxation parameter, contrast concentration parameter, or other information is already available, which facilitates producing a quantitative result. In some non-limiting embodiments, the one or more known signal evolutions are associated with known values of the concentration of the contrast agent in one or more volumes in the one or more known resonant species. In some non-limiting embodiments, the one or more known signal evolutions include a signal in which the concentration of the contrast agent in the one or more volumes in the one or more resonant species over time in the series of sequence blocks is associated with a linear function.

Referring now to FIG. 5, FIG. 5 is a flowchart of a non-limiting embodiment or aspect of a process 400 for generating information associated with a concentration of a contrast agent. In some non-limiting embodiments, one or more of the steps of process 500 are performed (e.g., completely, partially, etc.) by control system 120 (e.g., one or more devices of control system 120). In some non-limiting embodiments, one or more of the steps of process 500 are performed (e.g., completely, partially, etc.) by another device or a group of devices separate from or including control system 120, such as imaging system 110, user interface 130, injector 140, and/or external data system(s) 150 (e.g., one or more devices of imaging system 110, user interface 130, injector 140, and/or external data system(s) 150).

As shown in FIG. 5, at step 502, process 500 includes determining an input function (e.g., a blood pool input function, a patient transfer function, etc.) for a patient based on data associated with the patient, the input function providing a time enhancement output for a given input. For example, the input function can be determined based on systems and methods for determining input functions as described in U.S. Pat. Nos. 5,840,026, 6,385,483, and 8,295,914, assigned to the assignee of the present disclosure, the disclosures of which are incorporated herein by reference. In some non-limiting embodiments the input function is a blood pool input function associated with a concentration of a contrast agent (e.g., a blood pool contrast agent, a diffusible contrast agent, etc.) in a blood pool (and/or a volume being imaged) of a patient over time.

As further shown in FIG. 5, at step 504, process 500 includes determining a desired time enhancement output. For example, the desired time enhancement output can be associated with or based on the contrast related parameter. As an example, the desired time enhancement output can include at least one of the following: a concentration of a contrast agent in a volume in an object in a sequence block in a series of sequence blocks, the concentration of the contrast agent in the volume over time in the series of sequence blocks, the concentration of the contrast agent in the blood pool of the patient in the sequence block, the concentration of the contrast agent in the blood pool of the patient over time in the series of sequence blocks, a fraction of the volume in the object including the blood in the sequence block, the fraction of the volume in the object including the blood over time in the series of sequence blocks, the concentration of the contrast agent in an extracellular volume of the object, a fraction of the volume in the object including the extracellular volume in the sequence block, the concentration of the contrast agent in the extracellular volume of the object and the fraction of the volume in the object including the extracellular volume over time in the series of sequence blocks, and/or the like. In some non-limiting embodiments, the desired time enhancement output is determined based on a contrast related parameter associated with the series of sequence blocks. For example, the desired time enhancement output is determined based on achievement of a concentration of the contrast agent in the blood pool of the patient over time in the series of sequence blocks associated with and/or defined by the contrast related parameter.

As further shown in FIG. 5, at step 506, process 500 includes using the input function for the patient to determine an injection protocol input, wherein the injection protocol input is derived based on a time to achieve the desired time enhancement output. For example, the desired time enhancement output can be associated with the concentration the contrast agent in a blood pool of the patient over time, such as at least one of (i) a substantially constant concentration of a contrast agent in the blood pool of the patient over time, (ii) a substantially linear rate of change in the concentration of the contrast agent in the blood pool of the patient over time (iii) a time varying concentration of the contrast agent utilized to generate a signal evolution for MR fingerprinting, or any combination thereof. In some non-limiting embodiments, the substantially linear rate of change in the concentration of the contrast agent in the blood pool of the patient over time is a substantially linear increase, a substantially linear decrease, or a combination thereof, in the concentration of the contrast agent in the blood pool of the patient over time.

In some non-limiting embodiments, the injection protocol input is optimized to minimize a time to achieve the desired time enhancement output. For example, the injection protocol input can be optimized to minimize a time to achieve the substantially constant concentration of the contrast agent in the blood pool of the patient over time. For example, the injection protocol input is optimized to minimize a time to achieve the substantially linear rate of change in the concentration of the contrast agent in the blood pool of the patient over time. As an example, the injection protocol input can be determined using an analytical solution or using a numerical, constrained optimization technique, such as a weighted least-squared numerical optimization, and/or the like.

As further shown in FIG. 5, at step 508, process 500 includes controlling an injector to deliver the contrast agent based on the determined injection protocol input. For example, control system 120 controls injector 140 to deliver the contrast agent via a bolus injection according to an injection protocol based on the determined injection protocol input. As an example, control system 120 controls imaging system 110 to image the patient based on the determined injection protocol input (e.g., to start imaging when the desired time enhancement output is achieved according to the determined injection protocol input). In some non-limiting embodiments, the imaging includes one of the following: positron emission tomography (PET) imaging, computed tomography (CT) imaging, magnetic resonance (MR) imaging, single-photon emission computed tomography (SPECT) imaging, or any combination thereof.

It is noted that, unless indicated otherwise herein, it is the amount (e.g., atoms or milligrams) of contrast agent over time (e.g., per second) that is relevant in determining delivery of the contrast agent, because contrast fluids including contrast agents are available in different concentrations of the contrast agents. As described herein, in some non-limiting embodiments, delivery of the contrast agent can be controlled and/or varied by controlling or changing a flow rate with a constant concentration of the contrast agent. As further described herein, in some non-limiting embodiments, delivery of the contrast agent can be controlled and/or varied by varying a ratio of the contrast fluid and saline (or other diluent or flushing fluid) over time, for example, with a total volumetric flow rate that is constant over time.

Figure 6A:
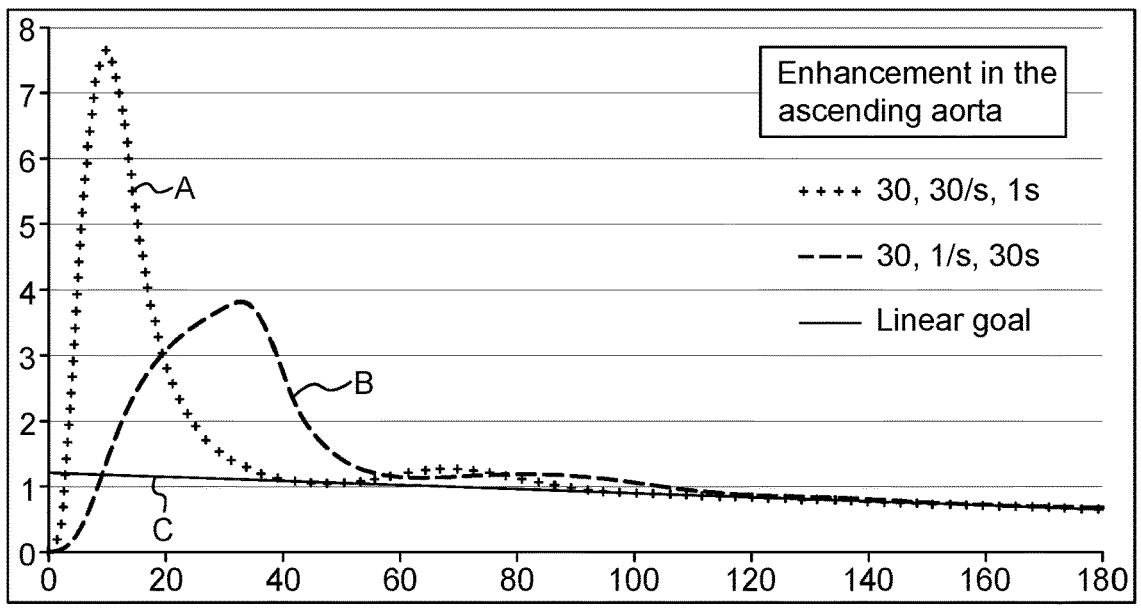
FIGS. 6A and 6B are graphs of example contrast agent concentrations in the ascending aorta of a patient in implementations of a non-limiting embodiment or aspect of a process described herein.
Figure 6B:
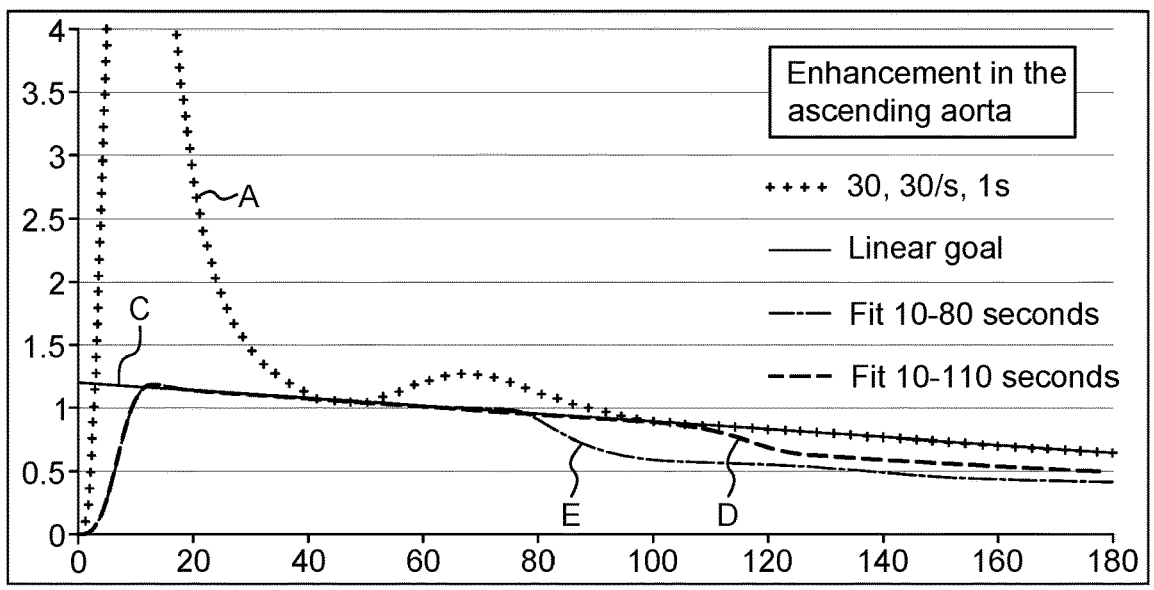
Figure 6C:
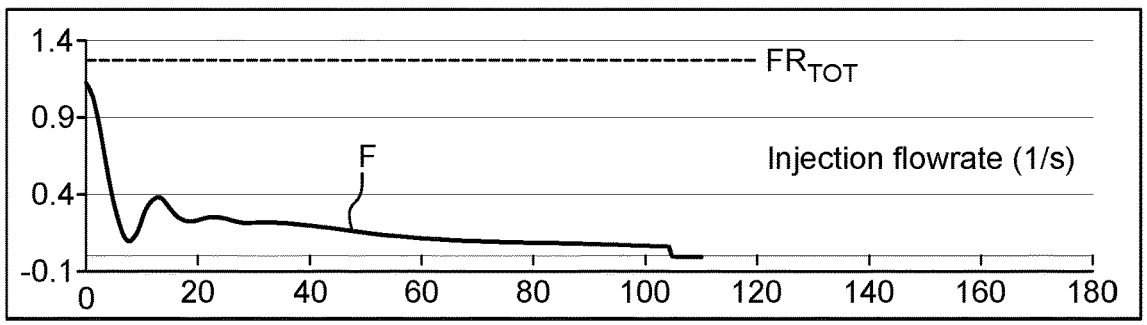
FIG. 6C is a graph of an example injection profile or flow rate over time in the implementations of FIG. 6B.

FIGS. 6A-6C show an example implementation of injection results and an example injection protocol produced by application of a process as described herein. FIGS. 6A and 6B represent a contrast agent concentration at the ascending aorta of the patient. FIG. 6C represents the injection profile or flow rate over time. Vertical units of the graphs are arbitrary because the vertical units depend on patient size, weight, contrast agent concentration, imaging modality sensitivity, and/or the like. Horizontal axis of the graphs of FIGS. 6A-6C are time in seconds. In FIG. 6A, curve A represents an enhancement produced by injecting a very high concentration of a contrast agent, for example 30 units, all in 1 second, at a sufficient total volumetric flow rate and with a saline flush sufficient to ensure timely transport of the bolus to the central circulation.

As shown in curve A in FIG. 6A, there is a rapid rise and fall to a first minimum of contrast agent concentration in the region of interest over 20 seconds to a somewhat stable decay starting at the first minimum at about 40 seconds. There is a slight rise or hump from about 60 to 80 seconds due to recirculation of the initial contrast pulse, followed by a continued long, slow decrease as the contrast agent diffuses into tissue, is metabolized, and/or is eliminated by the body. Curve A may be considered to be the impulse response of this patient and may be determined using a test bolus and measurement, or approximated by a physiological model, for example, as described herein. In FIG. 6A, curve B represents 30 units injected over 30 seconds, again with sufficient total volumetric flow rate and saline flush. After the recirculation humps have passed at about 120 seconds, curves A and B are essentially or substantially identical and represent the gradual decay due to diffusion, metabolism, and/or elimination. Because the 30 second injection happens over a longer time, the initial rise from 0 to 35 seconds is slower and the recirculation hump is similarly delayed and broadened. If a goal is to take an MR fingerprint image with a linearly decreasing contrast concentration, imaging is delayed at least 100 or 120 seconds after injection.

In FIG. 6B, a straight line C, for example, defined by the equation of a straight line, $y(t)=A*t+B$, is fit to the stably decaying segment of curve A. It may be desirable to generate an injection procedure or protocol that reaches this ramp indicated as straight line C in a practical and achievably rapid time, for example 10 seconds, using one or more of the models of determining patient input as described herein. FIG. 6C shows an example injection protocol or injection procedure input. Curve F is the injection procedure input or injection protocol flow rate over time. For example, curve F can be computed using the GRG Nonlinear Solving method in Microsoft Excel® to select the injection flow rate at each second while minimizing the least square error at each second over the time from 10 seconds to 110 seconds between the injection procedure input convolved with patient impulse response and the straight line C. This time range is useful if, for example, a scan time of 100 seconds were needed. The injection of injection procedure input F results in the concentration of the contrast agent as shown in curve D of FIG. 6B, Alternatively, an injection procedure may be computed to match the decay line C only until 80 seconds if a 70 second scan duration is all that is needed. For example, the injection can be the same as curve F, but drop to zero at about 74 seconds. Other longer or shorter durations may be similarly achieved. As is known to those skilled in the art, a GRG algorithm, convolution, and/or least square error computation may be implemented in other languages, for example, Matlab or C++ and on other computers, for example, as described herein with respect to FIG. 1, and/or other known algorithms for determining an injection input procedure can be used.

Line C may be a straight line of any slope and/or intercept. For example, if the slope of line C is 0 and the intercept is the total amount of blood pool contrast to be injected divided by the total blood volume anticipated, a resulting injection procedure input allows stable imaging of a blood pool contrast to commence in much less time than the 40 seconds needed to reach the first minimum or the 100 seconds to reach stable equilibrium after the recirculation hump or the 2 to 3 minutes often allowed. As mentioned herein, this time savings in scan time and patient time may be significant. Similarly, line C may have a positive slope, thus representing a rising concentration of contrast in the blood or tissue. While a generally rising contrast concentration may be achieved with a simple long constant injection of FIG. 4A, the stable linear region may be reached more quickly using the input function determining algorithm described herein.

In some non-limiting embodiments, an imaging method as described in U.S. patent application Ser. No. 14/123,390, filed on Apr. 6, 2012, issued as U.S. Pat. No. 9,436,989, assigned to the assignee of the present disclosure, the disclosure of which is incorporated herein by reference in its entirety, can be used to image a region or volume larger than is possible in a single acquisition (e.g., in a single NMR sequence block or series of sequence blocks). In some non-limiting embodiments, a voxel(s) in an imaged region that contains a blood vessel can be used to determine one or more parameters associated with the concentration of the contrast agent in the region, and the determined concentration of the contrast agent in the voxel(s) in the region can be applied to another voxel(s) in the region perfused by that vessel(s) with a similar time course of concentration of the contrast. As an example, the information associated with the volume in the object can include at least one of the following: the concentration of the contrast agent in blood in the volume over time, a fraction of the volume including blood over time, the concentration of the contrast agent in an extracellular volume of the patient over time, a fraction of the volume in the object including the extracellular volume over time, or any combination thereof, and control system 120 can estimate, based on the information associated with the volume in the object, for another volume in the object, at least one of the following: a concentration of the contrast agent in blood in the another volume over time, a fraction of the another volume including blood over time, the concentration of the contrast agent in another extracellular volume of the patient over time, a fraction of the another volume in the object including the another extracellular volume over time, or any combination thereof.

Figure 7A:
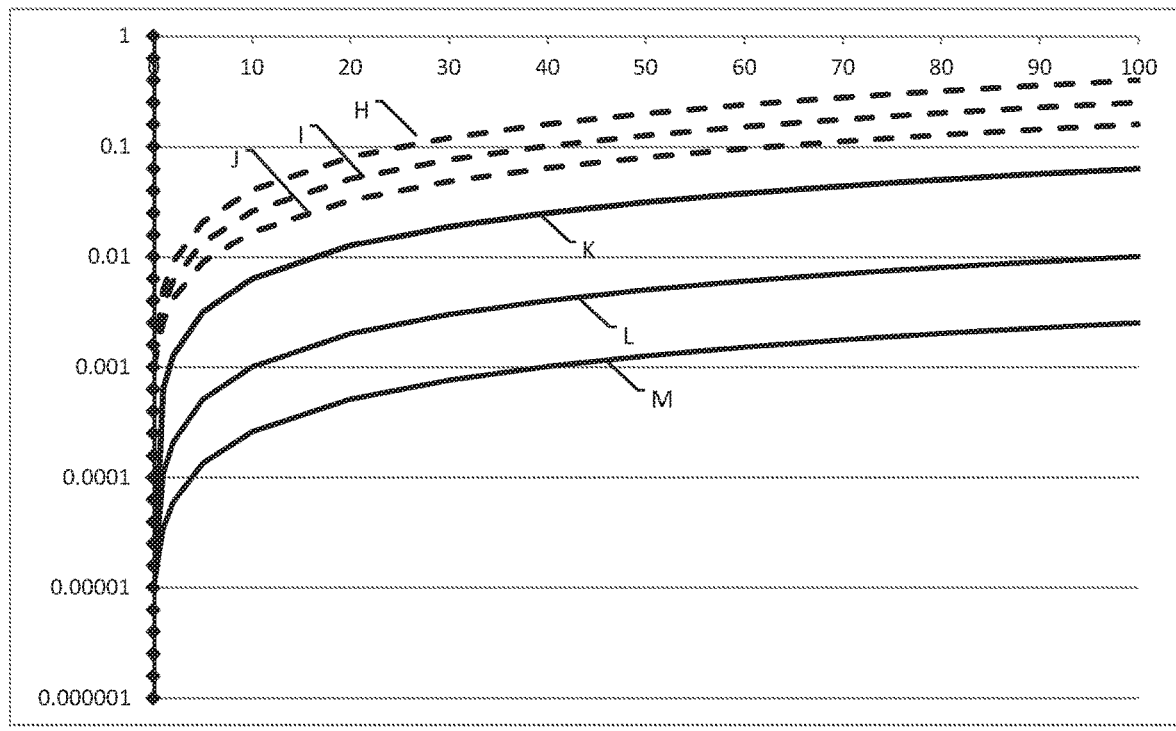
FIGS. 7A and 7B are graphs of example contrast related parameters of a signal evolution in implementations of a non-limiting embodiment or aspect of a process described herein.
Figure 7B:
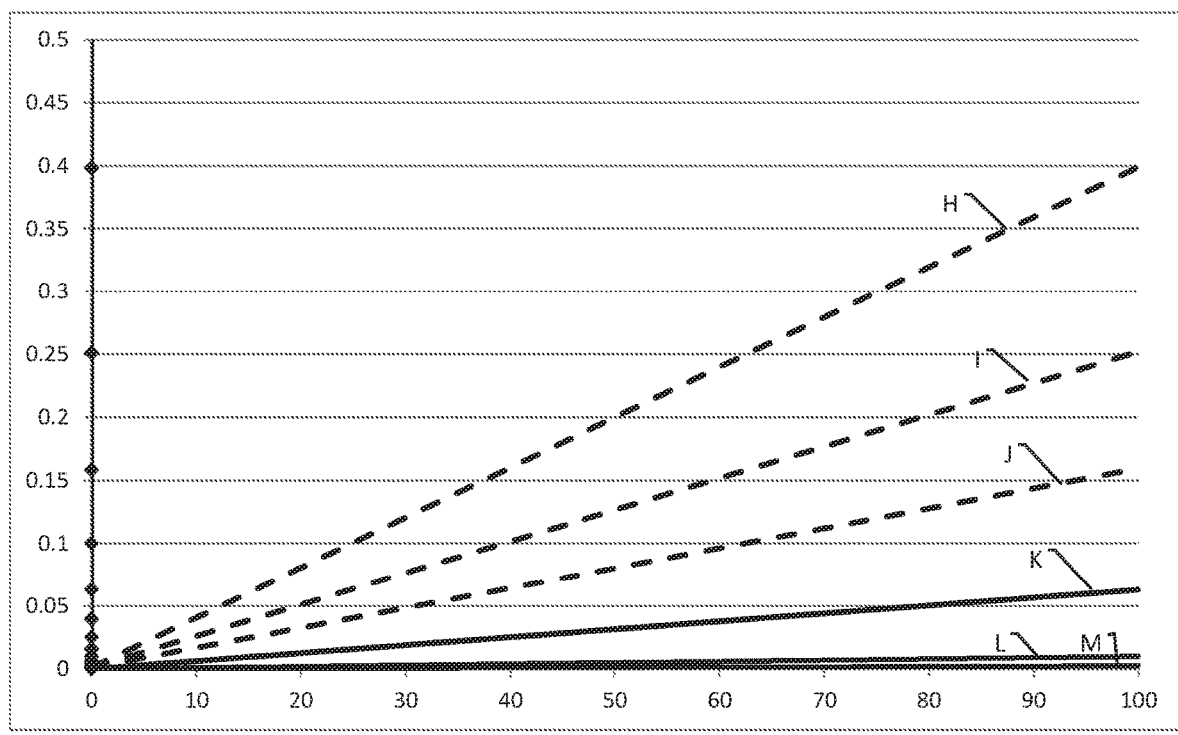

FIGS. 7A and 7B are graphs showing a contrast related parameter of a signal evolution implemented, modeled, and/or defined in a dictionary or library of MR signal evolutions in a database. There are multiple MR contrast fluids available from several manufacturers in a range of concentrations, for example, in a range of concentration of the contrast agent in the contrast fluid of about 0.25 to 1 mole/liter (M/l). Relaxivities of the MR contrast agents may vary, for example, from a relaxivity of about 4 to a relaxivity of about 10.

As described by Gulani et al., values for T1 and T2 that are incorporated into different signal evolutions have step sizes that vary depending upon the value of T1 and T2. Similarly, for incorporation of a contrast agent concentration in a volume of an object, which may cover multiple orders of magnitude, (e.g., 5 or t orders of magnitude, etc.), the steps can be made logarithmic, (e.g., 5 steps, 1, 0.63, 0.398, 0.251, 0.158, 0.1, for a contrast agent concentration which may cover 5 or 6 orders of magnitude). The logarithmic conversion may be repeated, for example, for 5 or 6 orders of magnitude down to 1E-6 M/l. Depending upon a magnet, coils, and other sources of noise in MRI, levels near or below this level are not likely to be distinguishable. As MRI equipment improves and/or higher magnetic fields are used for MRI, lower concentrations of the contrast agent can be modeled. An MR signal evolution can be created based on the logarithmic steps of the contrast agent concentration, for example, with each value of the contrast agent concentration or a parameter related to or associated with the contrast agent concentration, such as the contrast agent concentration multiplied by the relaxivity, and/or the like. The contrast agent concentration values are similar to T1 and T2 points along one of the dimensions or variables of the simulation used to create or generate the signal evolutions in the dictionary or library. The contrast agent concentration can be effectively modeled as a constant contrast agent concentration for very fast imaging sequences or sequence blocks, e.g., sequences on an order of seconds (e.g., a few seconds, etc.), other than the first pass of rapid bolus peaks. The contrast agent concentration may be modeled as a constant value if an injection protocol, as described herein, is used to achieve a relatively constant contrast concentration during an image scan time, for example, an image scan time of about 10 to 30 seconds, or after a sufficient time has elapsed for a substantially steady state concentration to be reached and the scan time is short compared to the diffusion, metabolism, and/or elimination of the contrast agent in a volume being imaged.

Modeling the contrast agent concentration with an arbitrary contrast agent concentration for each sequence block, for example, for an imaging protocol in which the contrast concentration may not be optimally modeled as a constant, the number of calculated signal evolutions expands greatly, it quickly becomes impossible to compute and the fit is significantly overdetermined or over constrained. However, in some non-limiting embodiments, because contrast agent concentration typically changes in a substantially gradual manner over time compared to the length of a sequence block, the contrast agent concentration is modeled as a linear concentration line over time. For example, a linear model of the contrast agent concentration over time includes two contrast related dimensions or parameters, which are added to the dictionary or library dimensions of a signal evolution. One parameter is the 0 time intercept and the other parameter is the slope over time.

FIGS. 7A and 7B show examples of linear models (e.g., lines) of a contrast agent concentration over time in a volume in an object in an implementation of a non-limiting embodiment or aspect of a process described herein. The data is the same in FIG. 7A as in FIG. 7B, but FIG. 7A uses a logarithmic vertical axis of contrast agent concentration in a volume of an object and FIG. 7B uses a linear vertical axis of contrast agent concentration in the volume of the object. The horizontal axes of FIGS. 7A and 7B indicate time. Diamond shaped markers on the vertical axes of FIGS. 7A and 7B indicate y intercept values of the linear contrast agent concentration. Lines H, I, and J have a y intercept of 0.001 and slopes of 0.003981072, 0.002511886, and 0.001584893 respectively. Lines K, L, and M have a y intercept of 1E-5 and slopes of 0.000630957, 0.0001, and 2.51189E-05 respectively. A similar set of lines may be created for other y intercept values used in a dictionary or library. Although not shown in FIGS. 7A and 7B, in some non-limiting embodiments, a set of lines with a negative slope are used to create signal evolutions for a dictionary or library which is employed in conjunction with the injection and imaging protocol as discussed herein in relation to FIGS. 6A-C. And, of course, a line with zero slope models or defines the constant contrast concentration discussed herein. In some non-limiting embodiments, a response of an MR signal may not depend linearly upon the contrast related parameter, e.g., the concentration of the contrast in the volume in the object, and that non-linearity is included in the detailed computation of each sequence block in a signal evolution.

In some non-limiting embodiments, an aspect of the line may be a decayed exponential (e.g., a contrast agent concentration can be modeled or defined by a line with a portion having a slope that decays exponentially), which may also be modeled using two variables (e.g., $y=A*\exp(-B*t)$). In some non-limiting embodiments, the contrast related parameter includes a growing exponential (e.g., $y=A(1-\exp(-B*t))$), which may model the contrast agent concentration in a volume in an object. In some non-limiting embodiments, more sophisticated, higher order lines with additional variables can be used. For example, use of additional variables is primarily limited by a computation time to create the dictionary or library of signal evolutions or fingerprints and a time to perform matching (e.g., convergence matching) for each volume or voxel. However, as computer power increases year over year, more and more sophisticated modeling of contrast related parameters becomes more practical.

The foregoing disclosure provides illustration and description, but is not intended to be exhaustive or to limit the implementations to the precise form disclosed. Modifications and variations are possible in light of the above disclosure or may be acquired from practice of the implementations.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code; it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features can be combined in ways not specifically recited in the claims and/or disclosed in the specification. Although each dependent claim listed below may directly depend on only one claim, the disclosure of possible implementations includes each dependent claim in combination with every other claim in the claim set.

Unless otherwise indicated, all ranges or ratios disclosed herein are to be understood to encompass any and all subranges or sub-ratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

All documents, such as but not limited to issued patents and patent applications, referred to herein, and unless otherwise indicated, are to be considered to be "incorporated by reference" in their entirety.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more," Where only one item is intended, the term "one" or similar language is used. Also, as used herein, the terms "has," "have," "having," and/or the like are intended to be open-ended terms. Further, the phrase "based on" is intended to mean "based, at least in part, on" unless explicitly stated otherwise.

What is claimed is:

1. A method comprising:
simulating, with a computer system comprising one or more processors, a plurality of parameters associated with one or more resonant species in a volume in an object using a model that simulates distribution of a contrast agent and behavior of the one or more resonant species in the volume in the object in response to magnetic resonance (MR) excitation being applied to the one or more resonant species over time in a series of sequence blocks, wherein, in each sequence block in the series of sequence blocks, the plurality of parameters occur simultaneously in the model that simulates the distribution of the contrast agent and the behavior of the one or more resonant species in the volume in the object, wherein at least one parameter of the plurality of parameters varies from the sequence block to another sequence block in the series of sequence blocks, and wherein the plurality of parameters include at least one contrast related parameter associated with a simulated concentration of the contrast agent in the model that simulates the distribution of the contrast agent and the behavior of the one or more resonant species in the volume in the object over time in the series of sequence blocks;
generating and storing, with the computer system, in association with the one or more resonant species in the volume in the object, in a database, a signal evolution based on the plurality of parameters simulated with the model, wherein the signal evolution defines the at least one contrast related parameter over time in the series of sequence blocks at two or more values, and wherein the at least one contrast related parameter defined by the signal evolution includes the simulated concentration of the contrast agent in the model that simulates the distribution of the contrast agent and the behavior of the one or more resonant species in the volume in the object over time in the series of sequence blocks;
controlling, with the computer system, an injector to deliver the contrast agent to a patient to provide, in a blood pool of the patient over time, a concentration of the contrast agent corresponding to the simulated concentration of the contrast agent as defined by the at least one contrast related parameter of the signal evolution stored in the database;
controlling, with the computer system, when the concentration of the contrast agent is provided in the blood pool of the patient over time as defined by the at least one contrast related parameter of the signal evolution stored in the database, a nuclear magnetic resonance (NMR) apparatus to apply radio frequency (RF) energy to a volume in the patient in another series of sequence blocks to expose the volume in the patient to MR excitation in the another series of sequence blocks, wherein the MR excitation in each sequence block in the another series of sequence blocks causes one or more resonant species in the volume in the patient to simultaneously produce individual signals in that sequence block;
controlling, with the computer system, the NMR apparatus to acquire the simultaneously produced individual signals in each sequence block in the another series of sequence blocks, wherein another signal evolution is determined based on the simultaneously produced individual signals acquired from each sequence block; and
matching, with the computer system, the another signal evolution to the signal evolution stored in the database to identify the one or more resonant species that produced the another signal evolution in response to the MR excitation being applied to the one or more resonant species.

2. The method of claim 1, wherein the at least one contrast related parameter is constant over time in the series of sequence blocks.

3. The method of claim 1, wherein the signal evolution defines the at least one contrast related parameter as a linear function.

4. The method of claim 1, further comprising:
determining, with the computer system, an input function for the volume in the object based on data associated with the object, the input function for the volume providing a time enhancement output for a given input, wherein the time enhancement output is associated with a time to achieve a desired concentration of the contrast agent over time in the volume in the object;
determining, with the computer system, a desired time enhancement output associated with the at least one contrast related parameter; and
using the input function for the volume to determine, with the computer system, the signal evolution defining the at least one contrast related parameter over time in the series of sequence blocks.

5. The method of claim 1, wherein the plurality of parameters further includes at least one of a spin lattice relaxation parameter T1, a spin-spin relaxation parameter T2, or any combination thereof.

6. The method of claim 1, wherein the at least one contrast related parameter further includes the concentration of the contrast agent in blood associated with the volume over time in the series of sequence blocks.

7. The method of claim 6, wherein the at least one contrast related parameter further includes a fraction of the volume including the blood over time in the series of sequence blocks.

8. The method of claim 7, wherein the at least one contrast related parameter further includes a fraction of the volume in the object including an extracellular volume over time in the series of sequence blocks.

9. The method of claim 1, wherein the at least one contrast related parameter changes at a linear rate over time in the series of sequence blocks.

10. The method of claim 9, wherein the at least one contrast related parameter is constant during the sequence block.

11. The method of claim 9, wherein the at least one contrast related parameter increases at a linear rate over a first subset of sequence blocks in the series of sequence blocks.

12. The method of claim 11, wherein the at least one contrast related parameter decreases at a linear rate over a second subset of sequence blocks in the series of sequence blocks.

13. The method of claim 1, further comprising:
determining, with the computer system, an input function for the patient based on data associated with the patient, the input function for the patient providing a time enhancement output for a given input;
determining, with the computer system, a desired time enhancement output based on the at least one contrast related parameter, wherein the desired time enhancement output is associated with the concentration of the contrast agent in the blood pool of the patient over time;
using the input function for the patient to determine, with the computer system, an injection protocol input, wherein the injection protocol input is derived based on a time to achieve the desired time enhancement output; and
controlling, with the computer system, the injector to deliver the contrast agent to the patient based on the determined injection protocol input, wherein controlling the injector to deliver the contrast agent to the patient based on the determined injection protocol input provides the concentration of the contrast agent in the blood pool of the patient over time as defined by the at least one contrast related parameter.

14. The method of claim 13, wherein the injection protocol input is optimized to minimize a time to achieve the desired time enhancement output.

15. A computing system comprising:
one or more processors programmed or configured to:
simulate a plurality of parameters associated with one or more resonant species in a volume in an object using a model that simulates distribution of a contrast agent and behavior of the one or more resonant species in the volume in the object in response to magnetic resonance (MR) excitation being applied to the one or more resonant species over time in a series of sequence blocks, wherein, in each sequence block in the series of sequence blocks, the plurality of parameters occur simultaneously in the model that simulates the distribution of the contrast agent and the behavior of the one or more resonant species in the volume in the object, wherein at least one parameter of the plurality of parameters varies from the sequence block to another sequence block in the series of sequence blocks, and wherein the plurality of parameters include at least one contrast related parameter associated with a simulated concentration of the contrast agent in the model that simulates the distribution of the contrast agent and the behavior of the one or more resonant species in the volume in the object over time in the series of sequence blocks;
generate and store, in association with the one or more resonant species in the volume in the object, in a database, a signal evolution based on the plurality of parameters simulated with the model, wherein the signal evolution defines the at least one contrast related parameter over time in the series of sequence blocks at two or more values, and wherein the at least one contrast related parameter defined by the signal evolution includes the simulated concentration of the contrast agent in the model that simulates the distribution of the contrast agent and the behavior of the one or more resonant species in the volume in the object over time in the series of sequence blocks;
control an injector to deliver the contrast agent to a patient to provide, in a blood pool of the patient over time, a concentration of the contrast agent corresponding to the simulated concentration of the contrast agent as defined by the at least one contrast related parameter of the signal evolution stored in the database;
control, when the concentration of the contrast agent is provided in the blood pool of the patient over time as defined by the at least one contrast related parameter of the signal evolution stored in the database, a nuclear magnetic resonance (NMR) apparatus to apply radio frequency (RF) energy to a volume in the patient in another series of sequence blocks to expose the volume in the patient to MR excitation in the another series of sequence blocks, wherein the MR excitation in each sequence block in the another series of sequence blocks causes one or more resonant species in the volume in the patient to simultaneously produce individual signals in that sequence block;

control the NMR apparatus to acquire the simultaneously produced individual signals in each sequence block in the another series of sequence blocks, wherein another signal evolution is determined based on the simultaneously produced individual signals acquired from each sequence block; and match the another signal evolution to the signal evolution stored in the database to identify the one or more resonant species that produced the another signal evolution in response to the MR excitation being applied to the one or more resonant species.

16. The computing system of claim 15, wherein the one or more processors are further programmed or configured to:

determine an input function for the volume in the object based on data associated with the object, the input function for the volume providing a time enhancement output for a given input, wherein the time enhancement output is associated with a time to achieve a desired concentration of the contrast agent over time in the volume in the object;

determine a desired time enhancement output associated with the at least one contrast related parameter; and use the input function for the volume to determine the signal evolution defining the at least one contrast related parameter over time in the series of sequence blocks.

17. The computing system of claim 15, wherein the one or more processors are further programmed or configured to:

determine an input function for the patient based on data associated with the patient, the input function for the patient providing a time enhancement output for a given input;

determine a desired time enhancement output based on the at least one contrast related parameter, wherein the desired time enhancement output is associated with the concentration of the contrast agent in the blood pool of the patient over time;

use the input function for the patient to determine an injection protocol input, wherein the injection protocol input is derived based on a time to achieve the desired time enhancement output; and control the injector to deliver the contrast agent to the patient based on the determined injection protocol input, wherein controlling the injector to deliver the contrast agent to the patient based on the determined injection protocol input provides the concentration of the contrast agent in the blood pool of the patient over time as defined by the at least one contrast related parameter.

18. The computing system of claim 15, wherein the plurality of parameters further includes at least one of a spin lattice relaxation parameter T1, a spin-spin relaxation parameter T2, or any combination thereof.

* * * * *

UNITED STATES PATENT AND TRADEMARK OFFICE
CERTIFICATE OF CORRECTION

PATENT NO. : 11,986,621 B2
APPLICATION NO. : 16/462410
DATED : May 21, 2024
INVENTOR(S) : Arthur E. Uber, III It is certified that error appears in the above-identified patent and that said Letters Patent is hereby corrected as shown below:

In the Specification

In Column 3, Line 18, delete "Clause 8" and insert -- Clause 8. --, therefor.
In Column 3, Line 45, delete "comprising;" and insert -- comprising: --, therefor.
In Column 4, Line 25, delete "concentration the" and insert -- concentration of the --, therefor.
In Column 5, Line 61, delete "interest," and insert -- interest. --, therefor.
In Column 6, Line 9, delete "identified, All" and insert -- identified. All --, therefor.
In Column 6, Line 18, delete "form" and insert -- from --, therefor.
In Column 10, Line 36, delete "coupled" and insert -- coupled to --, therefor.
In Column 12, Line 23, delete "remote" and insert -- remotely --, therefor.
In Column 12, Line 31, delete "printers," and insert -- printers. --, therefor.
In Column 12, Line 40, delete "thresholds," and insert -- thresholds. --, therefor.
In Column 14, Line 24, delete "blood stream" and insert -- bloodstream --, therefor.
In Column 14, Line 27, delete "(Ply)" and insert -- (PIV) --, therefor.
In Column 16, Line 59, delete "TGF)," and insert -- TOF), --, therefor.
In Column 17, Line 44, delete "determined a" and insert -- determined by a --, therefor.
In Column 18, Line 9, delete "y(t)=+B" and insert -- y(t)=A*t+B --, therefor.
In Column 19, Line 35, delete "generated" and insert -- generated by --, therefor.
In Column 22, Line 7, delete "al," and insert -- al. --, therefor.
In Column 22, Line 44, delete "al," and insert -- al. --, therefor.
In Column 23, Line 31, delete "level);" and insert -- level), --, therefor.
In Column 23, Line 56, delete "response;" and insert -- response, --, therefor.
In Column 24, Line 5, delete "Step 2," and insert -- Step 2. --, therefor.
In Column 29, Line 58, delete "systems;" and insert -- systems, --, therefor.
In Column 31, Lines 22-23, delete "in in the" and insert -- in the --, therefor.
In Column 32, Line 53, delete "concentration the" and insert -- concentration of the --, therefor.
In Column 34, Line 36, delete "FIG. 6B," and insert -- FIG. 6B. --, therefor.
In Column 36, Line 49, delete "or defines" and insert -- defines --, therefor.
In Column 37, Line 62, delete ""one or more,"" and insert -- "one or more." --, therefor.

Signed and Sealed this
Seventeenth Day of September, 2024

Katherine Kelly Vidal
*Director of the United States Patent and Trademark Office*